(12) United States Patent
Okubo et al.

(10) Patent No.: US 9,931,101 B2
(45) Date of Patent: Apr. 3, 2018

(54) CATHETER

(71) Applicant: TERUMO KABUSHIKI KAISHA, Shibuya-ku, Tokyo (JP)

(72) Inventors: Itaru Okubo, Ninomiya (JP); Kenta Mitsuhashi, Fujinomiya (JP); Yuuki Sakaguchi, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 313 days.

(21) Appl. No.: 14/947,729

(22) Filed: Nov. 20, 2015

(65) Prior Publication Data
US 2016/0143616 A1 May 26, 2016

Related U.S. Application Data

(63) Continuation of application No. PCT/JP2014/063038, filed on May 16, 2014.

(30) Foreign Application Priority Data

May 21, 2013 (WO) .................. PCT/JP2013/064051

(51) Int. Cl.
*A61B 8/12* (2006.01)
*A61M 39/10* (2006.01)
(Continued)

(52) U.S. Cl.
CPC ........... *A61B 8/12* (2013.01); *A61M 25/0097* (2013.01); *A61M 25/01* (2013.01); *A61M 39/10* (2013.01);
(Continued)

(58) Field of Classification Search
CPC ..... A61B 8/12; A61M 39/10; A61M 25/0097; A61M 25/01; A61M 2039/062; A61M 2025/0004
See application file for complete search history.

(56) References Cited

U.S. PATENT DOCUMENTS 6,364,841 B1    4/2002  White et al.
2007/0232892 A1*  10/2007  Hirota .................. A61B 5/0066
                                                              600/407
(Continued)

FOREIGN PATENT DOCUMENTS

JP          2002-360578 A    12/2002
JP          2011-152274 A     8/2011
(Continued)

OTHER PUBLICATIONS

International Search Report (PCT/ISA/210) dated Jun. 17, 2014, by the Japanese Patent Office as the International Searching Authority for International Application No. PCT/JP2014/063038.
Extended European Search Report dated Feb. 21, 2017, issued by the European Patent Office in corresponding European Application No. 14800887.3. (5 pages).
(Continued)

*Primary Examiner* — Bo J Peng
(74) *Attorney, Agent, or Firm* — Buchanan Ingersoll & Rooney PC

(57) ABSTRACT

A catheter includes a sheath that is inserted into a lumen; a drive shaft that transmits mechanical drive force; a hub that moves the drive shaft; an outer tube that is provided in the sheath on a proximal side and comprises a first connector at a proximal portion; an inner tube that can move inside the outer tube; a second connector that can be connected to and disconnected from the first connector and can receive the inner tube; a sheath connection portion that connects the sheath and the outer tube; and a protective tube that protrudes toward a distal side further than the inner tube, accommodates the drive shaft, can be inserted into the outer tube and the sheath, and can be pulled out of the outer tube together with the hub and the inner tube as the second connector is disconnected from the first connector.

20 Claims, 34 Drawing Sheets

(51) Int. Cl.
    *A61M 25/00*   (2006.01)
    *A61M 25/01*   (2006.01)
    *A61M 39/06*   (2006.01)
(52) U.S. Cl.
    CPC ............... *A61M 2025/0004* (2013.01); *A61M 2039/062* (2013.01)

(56) References Cited

U.S. PATENT DOCUMENTS

| | | | |
|---|---|---|---|
| 2011/0224650 A1* | 9/2011 | Itou | A61B 8/12 604/524 |
| 2012/0271174 A1 | 10/2012 | Iwahashi | |
| 2013/0331820 A1 | 12/2013 | Itou et al. | |
| 2014/0371598 A1 | 12/2014 | Okubo et al. | |

FOREIGN PATENT DOCUMENTS

| | | | |
|---|---|---|---|
| JP | 2011-188913 A | 9/2011 | |
| JP | 2012-050706 A | 3/2012 | |
| JP | 2012-223346 A | 11/2012 | |
| WO | WO 99/15078 A1 | 4/1999 | |
| WO | WO 2013-133356 A1 | 9/2013 | |

OTHER PUBLICATIONS

Office Action (Communication pursuant to Rules 70(2) and 70a(2) EPC) dated Mar. 10, 2017, by the European Patent Office in corresponding European Patent Application No. 14800887.3. (1 page).

\* cited by examiner

CATHETER

CROSS REFERENCES TO RELATED APPLICATIONS

This application is a continuation of International Application No. PCT/JP2014/063038 filed on May 16, 2014 and claims priority to International Application No. PCT/JP2013/064051 filed on May 21, 2013, the entire content of both of which is incorporated herein by reference.

TECHNICAL FIELD

The present invention relates to a catheter, and particularly relates to a catheter which is inserted into a lumen such as a blood vessel, a Vessel, and the like and acquires an image from the inside of the lumen.

BACKGROUND DISCUSSION

When examining a target lesion such as a blood vessel, a Vessel, and the like inside a body lumen, an ultrasound catheter which transmits and receives ultrasounds at the target lesion is used. The ultrasound catheter includes an imaging core that comprises a transducer unit which transmits and receives ultrasounds and a drive shaft which rotates the transducer unit, and a sheath that has the imaging core built in and is inserted into a lumen. The imaging core can move inside the sheath in an axial direction.

Generally, when using the ultrasound catheter, an introducer sheath for providing access to the inside of the lumen is indwelled, and a guiding catheter is inserted into the lumen via the introducer sheath. Thereafter, a guide wire is inserted through the guiding catheter until the guide wire reaches a target place, and the ultrasound catheter is inserted along the guide wire to a site deeper than the target lesion. Then, from a state where the imaging core is disposed inside the sheath on a distal side, only the imaging core is caused to move backward and to pass through the target lesion while leaving the sheath behind. Since the transducer unit moves from the deep site while passing through the target lesion by moving only the imaging core backward, it is possible to observe ultrasound images which are continuously acquired through the front and the rear of the target lesion, and to generate three-dimensional data of shapes of a blood vessel, a Vessel, or the like.

In order to facilitate the imaging core to move in the axial direction inside the sheath, for example, the ultrasound catheter disclosed in International Application Publication No. WO 1999/015078 comprises a nested structure for extending and contracting in the axial direction provided in the sheath on a proximal side, the imaging core inside the sheath is caused to move in the axial direction with respect to the sheath by varying the overall length of a catheter main body.

Then, in the ultrasound catheter disclosed in International Application Publication No. WO 1999/015078, a connection portion which is connectable and disconnectable is provided between the sheath and the nested structure, and the imaging core can be pulled out of the catheter main body in accordance with a situation.

SUMMARY

There may be a situation that the ultrasound catheter disclosed in the aforementioned international application publication is sometimes caught by a complicatedly curved blood vessel, a stenosed blood vessel, a stent embedded inside a blood vessel, or the like when being inserted into a blood vessel, thereby being difficult to be pulled out of the blood vessel. In such a case, an imaging core is removed from the inside of a sheath, and a medical instrument, for example, a guide wire (hereinafter, suitably abbreviated to the wire) or the like having rigidity higher than that of the imaging core is inserted in place thereof, and thus the sheath is likely to be pulled out.

However, when the imaging core is intended to be pulled out in the ultrasound catheter disclosed in the aforementioned international application publication is, since a connection portion which is connectable and disconnectable is provided between the sheath and a nested structure, in a state where the ultrasound catheter is inserted into a guiding catheter, the connection portion approaches a Y-connector which is connected to the guiding catheter on a proximal side. Since the guide wire has been also led from the Y-connector, there may be a possibility that the guide wire and the connection portion interfere with each other, and it is difficult to control the guide wire when operating the ultrasound catheter, resulting in degradation of the operability. Moreover, since the connection portion approaches the Y-connector, there may be a possibility of confusion between blood flowing out from the connection portion and blood flowing out from the Y-connector after the imaging core is extracted, resulting in an erroneous operation. Furthermore, as the connection portion approaches the Y-connector, there may be a possibility that blood flowing out of the connection portion flows into the valve body which is provided in the Y-connector, from the outside, resulting in degradation of the operability.

The catheter disclosed here has been made to address the aforementioned problems. The disclosed catheter comprises a connectable and disconnectable portion and comprises high operability.

A catheter includes: a sheath configured to be inserted into a lumen in a living body; a drive shaft positioned in the sheath to transmit a mechanical drive force; an axially movable hub connected to the drive shaft so that axial movement of the hub results in axial movement of the drive shaft; an outer tube positioned proximal of the sheath and comprising a first connector at a proximal portion of the outer tube; and an axially movable inner tube positioned at least partially inside the outer tube and being connected to the hub to axially move together with the hub relative to the outer tube. The inner tube projects distally from the hub and possesses a distal end. A second connector is configured to be connected to and disconnected from the first connector and comprises a pass-through port configured to receive the inner tube, a sheath connection portion connects the sheath and the outer tube; and a protective tube protrudes distally beyond the distal end of the inner tube. The drive shaft is accommodated in the protective tube, and the protective tube is positionable inside the outer tube and inside the sheath, and is removable from inside the outer tube and the sheath together with the hub and the inner tube after the second connector is disconnected from the first connector.

In a catheter having a configuration described above, since a second connector provided in an outer tube on a proximal side is disconnectable, the second connector is disposed away from an insertion target, for example, a Y-connector or the like during an operation. Therefore, even when it becomes difficult to pull out the catheter from the inside of a blood vessel, the second connector can be disconnected without interfering with a guide wire which has been led from the insertion target, and the guide wire at a distant position is easily controlled, thereby improving the operability of the guide wire and the catheter. In addition, since the second connector is away from the insertion target interposing the outer tube therebetween, blood flowing out of the second connector is unlikely to be mistaken for blood flowing out of the insertion target, and an operation can be performed while confirming the blood is flowing out, thereby improving the operability. In addition, since the second connector is away from the insertion target interposing the outer tube therebetween, blood flowing out of the second connector is unlikely to enter the insertion target from the outside, thereby improving the operability. Then, since there is provided a protective tube which protrudes toward a distal side further than the inner tube, accommodates the drive shaft, and can be inserted into the outer tube and the sheath, the drive shaft can be prevented from bending or the like on account of the protective tube when the inner tube is thrust into or drawn out of the outer tube, and there is no need to insert a wire or the like through the protective tube when the wire or the like is inserted into the sheath, by disconnecting the second connector from a first connector and pulling out the protective tube from the outer tube together with a hub and the inner tube, thereby improving the operability.

If an engagement portion having an enlarged outer diameter is provided in a distal portion of the inner tube, even when the inner tube is drawn out to the fullest extent from the outer tube in a proximal end direction, the engagement portion is caught by the second connector, and thus, the inner tube can be prevented from coming out.

Providing the sheath connection portion with a seal member which comes into contact with an outer circumferential surface of the protective tube in a slidable manner prevents blood from leaking from a lumen of the sheath to the outer tube. Moreover, if a passage allowing the protective tube and the drive shaft to be inserted therethrough is shut by the seal member as the protective tube and the drive shaft are pulled out, blood is prevented from leaking via the lumen of the sheath, thereby improving the safety, and blood does not leak on the hand-side of an operator, thereby improving the operability as well. In addition, since the outer tube is provided on the proximal side of the sheath connection portion and proximal of seal member, blood leaking from the seal member does not reach the outside unless the blood passes through the outer tube further. Therefore, blood is more reliably prevented from leaking via the sheath.

The protective tube may be fixed to the inner tube, whereby the protective tube can be moved in accordance with a movement of the inner tube.

The protective tube may alternatively be fixed to the hub, whereby the protective tube can be moved in accordance with a movement of the hub.

If the protective tube is a tubular body which is impermeable to liquid, priming liquid such as blood, physiological saline solution, and the like circulating the inside of the protective tube does not leak into the outer tube via the protective tube. As a result, since there is no need to inject the priming liquid into a portion of the outer tube (the volume of priming processing is lessened), it is possible to improve the operability, and since air remaining inside the protective tube can be reduced, it is possible to shorten the preparation time when in use. In addition, since liquid such as blood, physiological saline solution, and the like does not leak into the outer tube, there is no need to provide the seal member between the outer tube and the inner tube. Then, as liquid such as blood, physiological saline solution, and the like is prevented from leaking into the outer tube, the liquid is more reliably prevented from leaking out further than the outer tube.

The inner circumferential surface of at least one of the outer tube and the sheath connection portion can be provided with a slope portion which slopes toward an axial center in distal direction, whereby the wire, the drive shaft, the protective tube, and the like inserted through the outer tube can be smoothly guided into the sheath along the slope portion.

According to another aspect, a catheter comprises: a sheath configured to be inserted into a lumen in a living body, with the sheath possessing a proximal portion; a drive shaft positioned in the sheath to transmit a mechanical drive force; an axially movable hub connected to the drive shaft so that axial movement of the hub results in axial movement of the drive shaft; an outer tube positioned proximal of the sheath, with the drive shaft passing through the outer tube, and the outer tube possessing a proximal portion at which is located a first connector; an axially movable inner tube connected to the hub to axially move together with the hub relative to the outer tube, with the inner tube being positioned inside the outer tube and projecting in a distal direction from the hub; and a second connector connected to and disconnectable from the first connector. The second connector comprises a pass-through port, and the inner tube and the drive shaft both pass through the pass-through port of the second connector. A sheath connection portion connects the proximal portion of the sheath and the distal portion of the outer tube, with the drive shaft passing through the sheath connection portion. A protective tube is fixed to and axially movable together with one of the hub and the inner tube, and the protective tube axially overlaps and surrounds a portion of the drive shaft, with the protective tube possessing an outer peripheral surface and a distal end that protrudes distally beyond a distal end of the inner tube. The drive shaft is accommodated in the protective tube, and the protective tube is positioned inside the outer tube and is removable from inside the outer tube together with the hub and the inner tube after the second connector is disconnected from the first connector. A seal is in sealing contact with the outer peripheral surface of the protective tube, and the drive shaft passes through the seal, with the protective tube and the drive shaft being removable from the seal.

In accordance with another aspect, a method comprises: inserting a sheath of a catheter into a lumen in a living body, wherein the sheath possesses a lumen extending along a length of the sheath. The catheter also includes: a drive shaft positioned in the lumen of the sheath to transmit a mechanical drive force; an outer tube positioned proximal of the sheath and comprising a first connector at a proximal portion of the outer tube, with the outer tube possessing a lumen; an axially movable inner tube positioned at least partially inside the outer tube, with the inner tube possessing a distal end; a second connector connected to the first connector and comprising a pass-through port through which the inner tube and the drive shaft pass; a sheath connection portion connecting the sheath and the outer tube; and a protective tube protruding distally beyond the distal end of the inner tube, with the protective tube surrounding a portion of the drive shaft, and the protective tube being positioned inside the outer tube and inside the sheath. The method further comprises: moving the sheath to a target site in the living body; disconnecting the second connector from the first connector while the sheath remains in the living body; proximally moving the drive shaft, the inner tube and the protective tube relative to the outer tube to remove the drive shaft, the inner tube and the protective tube from the outer tube while the sheath remains in the living body; inserting a wire into the outer tube while the sheath remains in the living body; and axially moving the wire through the outer tube, through the sheath connection portion and into the lumen of the sheath while the sheath remains in the living body.

DETAILED DESCRIPTION

Figure 1:
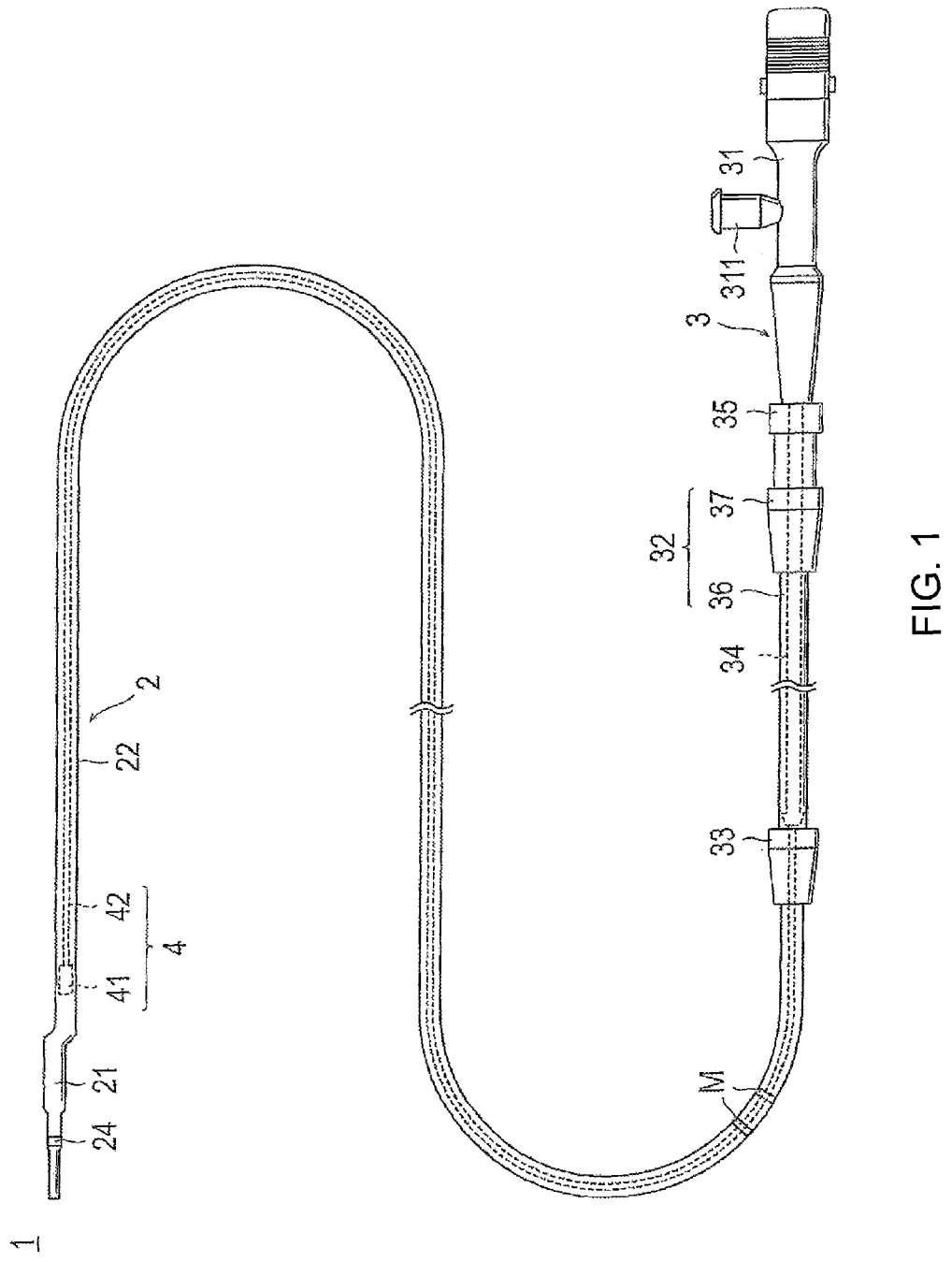
FIG. 1 is a plan view illustrating an ultrasound catheter in a first embodiment.

Hereinafter, embodiments of a catheter, representing examples of the inventive catheter disclosed here, will be described with reference to the drawings. Dimensional ratios in the drawings are exaggerated for convenience of descriptions, and thus, the dimensional ratios may be different from the actual ratios.

Figure 2:
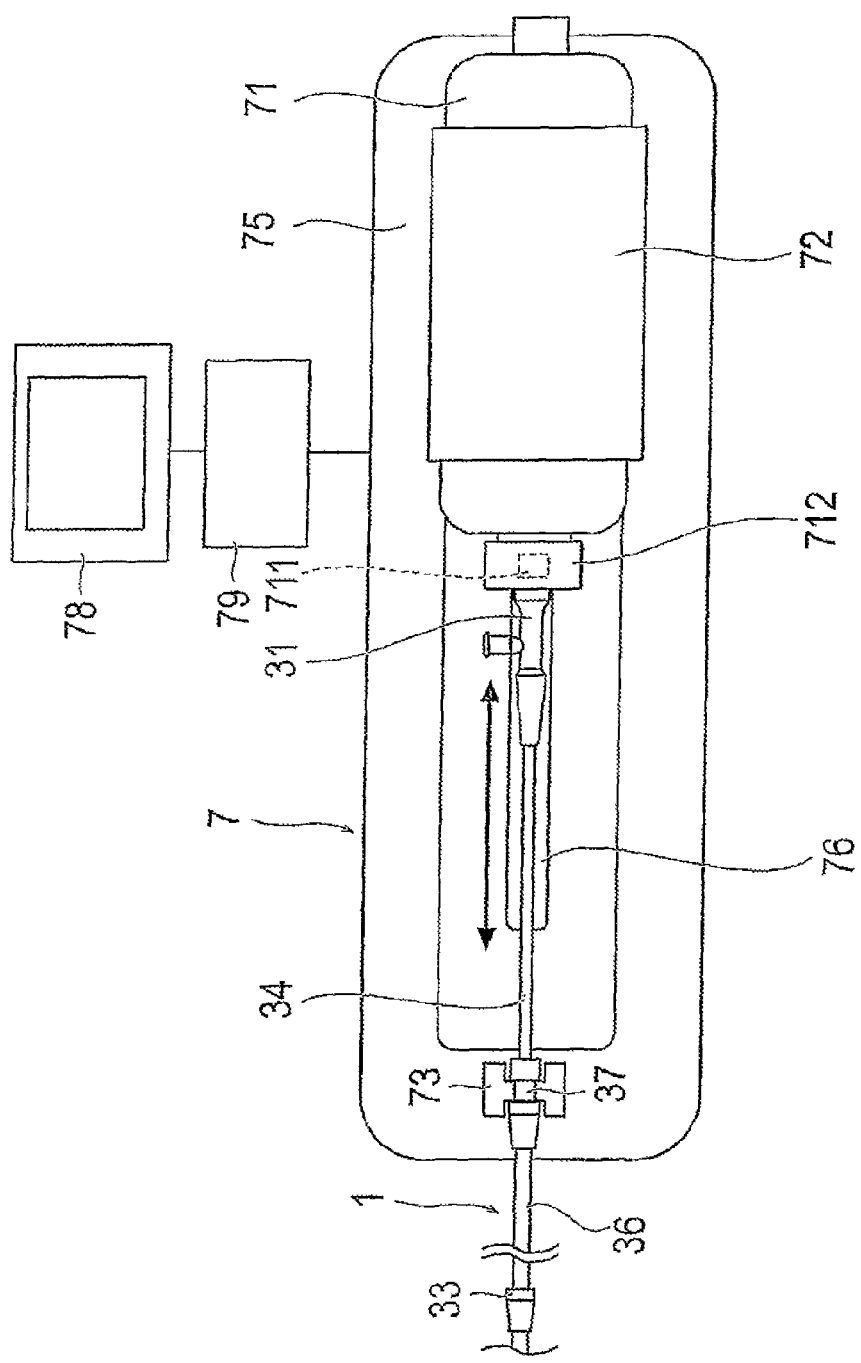
FIG. 2 is a schematic plan view illustrating an intraluminal diagnosis system which comprises the ultrasound catheter in the first embodiment.

A catheter according to a first embodiment is an ultrasound catheter 1 which is mainly adopted for diagnosing a state of the inside of a blood vessel through images by being inserted into the blood vessel. As illustrated in FIG. 1, an imaging core 4 for performing an ultrasound diagnosis is accommodated inside the ultrasound catheter 1. As illustrated in FIG. 2, the ultrasound catheter 1 is used by being connected to an external drive apparatus 7 which holds the ultrasound catheter 1 and drives the imaging core 4. In this Description, an end or side inserted into a lumen is referred to as "the distal end" or "the distal side", and a hand-side on which operations are performed is referred to as "the proximal end" or "the proximal side".

Figure 3:
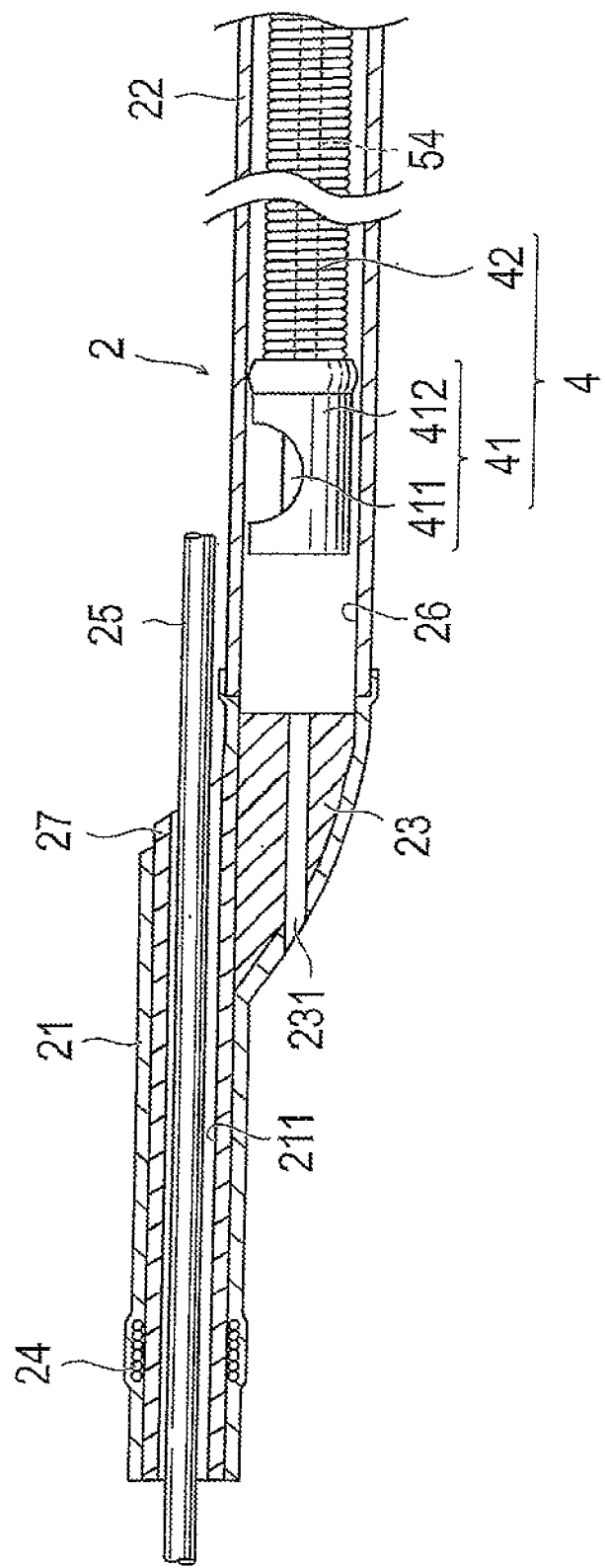
FIG. 3 is a cross-sectional view in a longitudinal direction illustrating a distal portion of the ultrasound catheter in the first embodiment.

As illustrated in FIGS. 1 to 3, the ultrasound catheter 1 comprises a sheath 2 which is configured to be inserted into a lumen of a living body, the imaging core 4 which transmits and receives ultrasounds with respect to a tissue inside the lumen, and an operation unit 3 which is positioned on the proximal side from the sheath 2 while allowing the imaging core 4 to penetrate.

The sheath 2 includes a sheath distal portion 21, a sheath tube 22, and a filling liquid inflow and outflow path member 23.

The sheath distal portion 21 is provided with a tubular sheath distal end member 27 in which a guide wire lumen 211 is formed or located, and an X-ray contrast marker 24 which is provided at a portion slightly closer to the proximal side than the distal portion. As a guide wire 25 to be inserted into a lumen in the living body passes through the guide wire lumen 211 in advance, the ultrasound catheter 1 can be guided to a target lesion along the guide wire 2. The X-ray contrast marker 24 is provided so as to be able to confirm a distal end position of the ultrasound catheter 1 through radioscopy when being inserted into the lumen. The ultrasound catheter 1 has "a rapid-exchange structure" in which the guide wire lumen 211 is provided at only the distal portion. The ultrasound catheter 1 has a structure in which the guide wire lumen 211 does not exist within the range of image-capturing performed by the imaging core 4 so as to prevent image capturing from being hindered by the guide wire lumen 211. That is the guide wire lumen 211 does not axially overlap the range of image-capturing performed by the imaging core 4.

A priming lumen 231 is formed in the filling liquid inflow and outflow path member 23. The priming lumen 231 is a hole which communicates with a lumen 26 inside the sheath tube 22 and through which physiological saline solution filling the inside of the sheath tube 22 flows to the outside.

The imaging core 4 is positioned in the sheath 2 and is movable in the axial direction of the sheath 2 in a slidable manner. The imaging core 4 comprises a transducer unit 41 for transmitting and receiving ultrasounds toward a tissue inside the lumen, and a drive shaft 42 having the transducer unit 41 attached to the distal end of the drive shaft 42 to rotate the transducer unit 41. The transducer unit 41 is configured to include an ultrasound transducer 411 (an image information acquisition portion) which transmits and receives ultrasounds, and a housing 412 which accommodates the ultrasound transducer 411.

The sheath tube 22 is fabricated from a material that is highly permeable to ultrasounds. A portion within a range in which the ultrasound transducer 411 of the sheath 2 moves is configured to be an acoustic window portion where ultrasounds permeate. A marking portion M is provided on the surface of the sheath tube 22 so that an operator can confirm a length of the sheath 2 which is thrust into or positioned in the lumen. The sheath tube 22 has a one-layer structure in the present embodiment. However, the sheath tube 22 may have a multi-layer structure.

The drive shaft 42 is flexible and has properties configured to transmit rotational power, which is applied from the external drive apparatus 7 (refer to FIG. 2) to the operation unit 3, to the transducer unit 41. For example, the drive shaft 42 is configured to be a multi-layer coiled tubular body having three layers of coils or the like which are alternately coiled in right-left-right winding directions. The transducer unit 41 rotates as the drive shaft 42 transmits rotational power so that a 360-degree observation can be performed on a target lesion inside a lumen such as a blood vessel, a Vessel, and the like. In addition, a signal line 54 for sending a signal detected by the transducer unit 41 to the operation unit 3 passes through or extends along the inside of the drive shaft 42.

The operation unit 3 includes a hub 31 having a port 311 through which physiological saline solution used for performing air bleeding is injected, an outer tube 32 which is provided in the sheath 2 on the proximal side of the sheath 2 and is fixed to the sheath 2, a relay connector 33 (a sheath connection portion) which connects the outer tube 32 and the sheath 2, a second connector 35 which can be connected to and disconnected from the outer tube 32 on the proximal side of the outer tube, and an inner tube 34 which is fixed to the hub 31 on the distal side of the hub 31 and moves relative to or with respect to the outer tube 32 inside the outer tube 32 in accordance with a movement of the hub 31. The outer tube 32 includes an outer tube main body 36 which is fixed to the relay connector 33 on the distal side of the outer tube main body 36, and a unit connector 37 which is fixed to the outer tube main body 36 on the proximal side of the outer tube main body 36 and is configured to be connected to and disconnected from the second connector 35.

Figure 5:
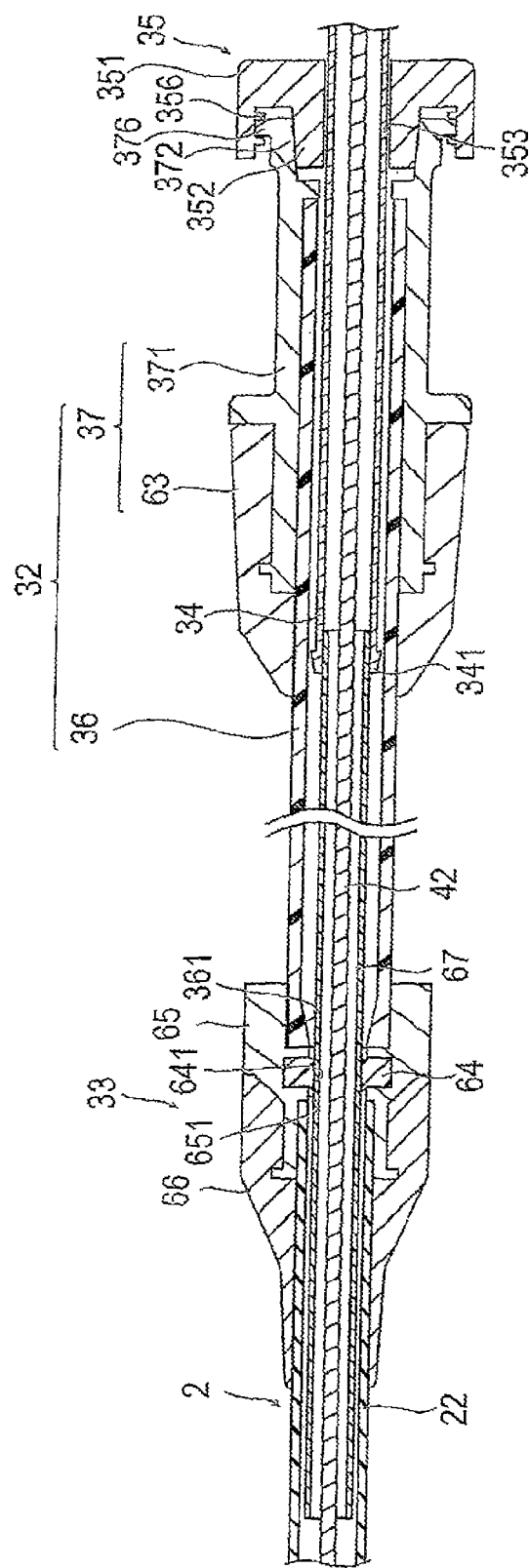
FIG. 5 is a cross-sectional view in the longitudinal direction illustrating a unit connector and a relay connector of the ultrasound catheter in the first embodiment.

As illustrated in FIG. 5, the inner circumferential surface of the outer tube main body 36 includes a tapered slope portion 361 which slopes toward the axial center in a direction toward the distal end, and the tapered slope portion 361 is located at the distal end portion of the outer tube main body 36 that axially overlaps and is fixed to the relay connector 33.

The hub 31 holds the drive shaft 42 and the inner tube 34. As the inner tube 34 is thrust into or drawn out of the outer tube 32 which is configured to include the unit connector 37 and the outer tube main body 36, the drive shaft 42 slides in the axial direction inside the operation unit 3 and the sheath 2 in association with the inner tube 34.

When the inner tube 34 is thrust in all the way to the end, as illustrated in FIG. 1, the end portion of the inner tube 34 on the distal side arrives at the vicinity of the end portion of the outer tube 32 on the distal side, that is, the vicinity of the relay connector 33. Then, in the aforementioned state, the transducer unit 41 is positioned in the vicinity of the distal end of the sheath tube 22 of the sheath 2.

Figure 4:
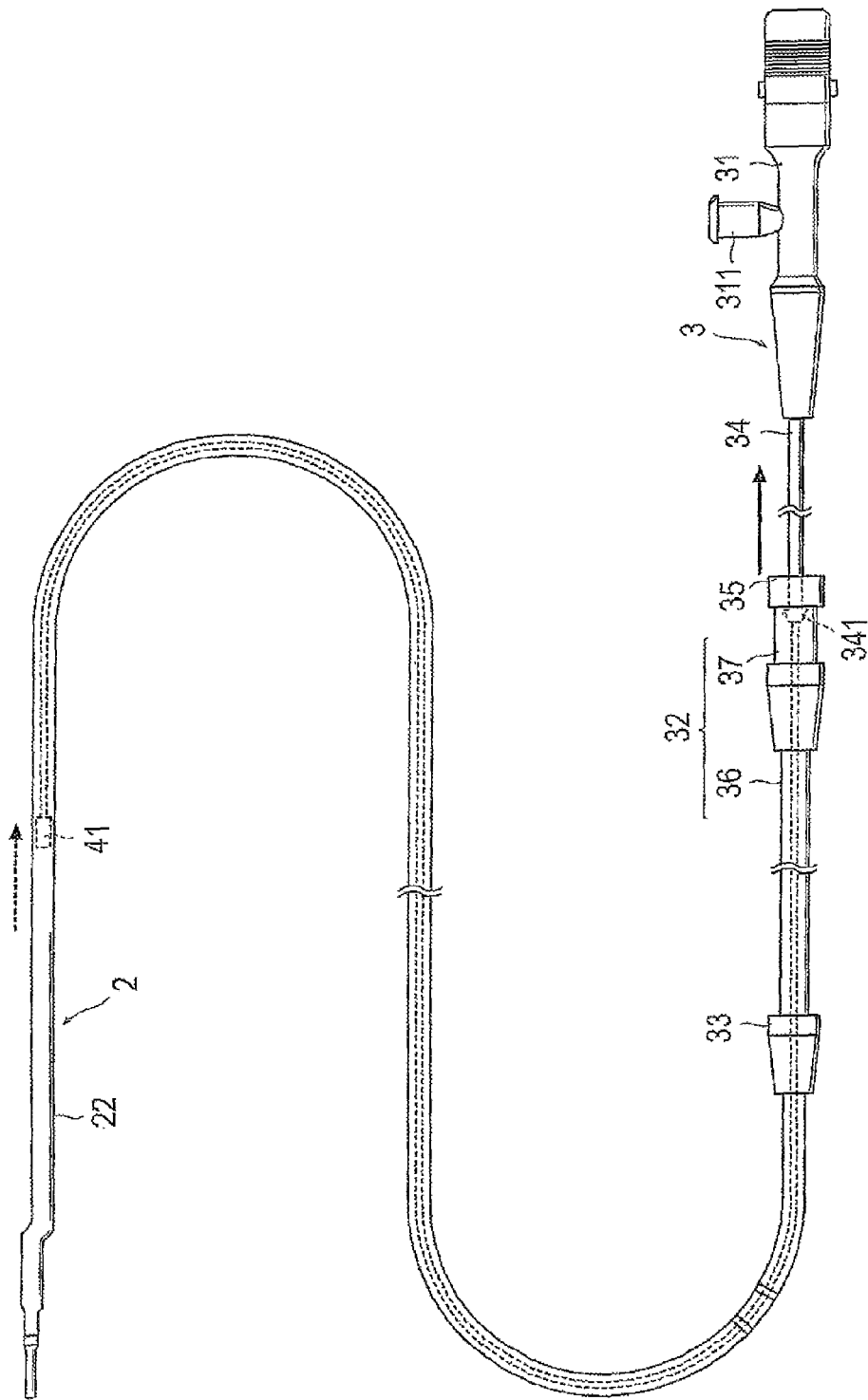
FIG. 4 is a plan view illustrating the ultrasound catheter in a state where a transducer unit is pulled back.

In addition, as illustrated in FIG. 4, when the inner tube 34 is drawn out to the fullest extent, a stopper 341 (an engagement portion) of the inner tube 34 having an enlarged outer diameter (enlarged relative to an immediately adjoining portion of the inner tube 34) and located at the distal end of the inner tube 34 is caught by the inner wall of the second connector 35. Thus, the inner tube 34 excluding the vicinity of the caught distal end portion is exposed on the proximal side of the second connector 35. Then, in the aforementioned state, the transducer unit 41 is caused to return through the inside of the sheath 2 while leaving the sheath 2 behind so that only the transducer 41 is retracted or drawn-out. As the transducer unit 41 rotates and moves, a tomographic image of a blood vessel, a Vessel, or the like can be generated.

As illustrated in FIG. 5, a protective tube 67 is fixed to the inner circumferential surface of the distal portion of the inner tube 34 through which the drive shaft 42 passes. The drive shaft 42 is accommodated inside the protective tube 67. The protective tube 67 extends distally beyond the distal end of the inner tube 34 and is slidable in the axial direction inside the outer tube 32 and inside the sheath tube 22. Therefore, when the inner tube 34 is thrust into and moved along the outer tube 32, the protective tube 67 is also thrust into and moved in a direction in which the inner tube 34 is thrust and moved. Then, the drive shaft 42 which is positioned inside the outer tube 32 and extends distally on the distal side from the inner tube 34 is covered with the protective tube 67 inside the outer tube 32. In other words, inside the outer tube 32 whose inner diameter is greater than the outer diameter (and inner diameter) of the inner tube 34 so as to accommodate the inner tube 34 inside the outer tube 32, the drive shaft 42 is accommodated inside the protective tube 67 whose inner diameter is smaller than the inner diameter of the outer tube 32. Therefore, when the inner tube 34 is thrust into (moved axially forward) or drawn out of the outer tube 32, the drive shaft 42 is covered by the protective tube 67, and the protective tube 67 can prevent the drive shaft 42 from being bent or the like.

The protective tube 67 may be a tubular body which is impermeable to liquid and is formed with a wall surface having no openings, instead of being formed as a coil or the like which allows water to permeate. In this case, the protective tube 67 can guide physiological saline solution, which is supplied through the port 311 of the hub 31, to the inside of the sheath tube 22 without allowing the physiological saline solution to flow into the outer tube 32. Examples of materials which can be used to fabricate the protective tube 67 include polyimide, blade containing polyimide, PTFE, polyethylene, polyamide, or the like. However, the material is not limited to these listed materials.

The unit connector 37 includes a unit connector main body 371 and a cover member 63. A tapered female connector 372 (a first connector) and a male screw portion 376 which is formed on the outer circumference of the female connector 372 are provided at the proximal end portion of the unit connector main body 371.

The second connector 35 includes a connection portion main body 351 connected to the female connector 372 of the unit connector 37 in a liquid-tight manner. The connection portion main body 351 includes a disconnectably tapered male connector 352 and a female screw portion 356 which is formed in the outer circumference of the male connector 352. The female connector 372 and the male connector 352 comprise a luer taper structure in which a predetermined gradient is formed so as to exhibit high sealing performance. The unit connector main body 371 and the second connector 35 are fixed to each other by screwing the male screw portion 376 into the female screw portion 356 so that it is possible to firmly maintain a state where the male connector 352 is connected to the female connector 372 in a liquid-tight manner. In other words, the female connector 372 and the male connector 352 have a lock-type luer taper structure comprising a screw-type lock mechanism which is configured to include the male screw portion 376 and the female screw portion 356. A pass-through port 353 which the inner tube 34 slidably penetrates is provided in the second connector 35. The pass-through port 353 has an inner bore diameter smaller than the outer diameter of the stopper 341 so that the stopper 341 cannot pass through or move proximally past the pass-through port 353.

The outer tube main body 36 attached to the relay connector 33 is inserted into and fixed to the unit connector main body 371, and the inner tube 34 extending from the hub 31 is inserted into (positioned in) the outer tube main body 36. The cover member 63 is combined with the unit connector main body 371, thereby holding the outer tube main body 36.

In addition, since the inner tube 34 extending from the hub 31 includes the stopper 341 (the engagement portion) which is located at the distal end of the inner tube 34, even when the hub 31 is pulled to the fullest extent, that is, even when the inner tube 34 is drawn out to the fullest extent from the outer tube 32, the stopper 341 is caught by the end surface of the second connector 35 on the distal side, and thus, the inner tube 34 does not slip out of the unit connector 37.

The relay connector 33 includes an outer tube holding portion 65, an anti-kink protector 66, and a seal member 64 (seal).

The outer tube holding portion 65 holds the outer tube main body 36. In addition, the proximal end portion of the sheath tube 22 is joined to the inner surface of the outer tube holding portion 65, and a passage 651 for guiding the drive shaft 42 and the protective tube 67 into the sheath tube 22 through the outer tube 32 is formed in the end portion of the outer tube holding portion 65. The smallest inner diameter of the tapered slope portion 361 at the distal end portion of the outer tube main body 36 is substantially the same as the inner diameter of the passage 651, thereby helping to smoothly guide a guide wire or the like, which is inserted through the outer tube 32, into the sheath tube 22. In addition, when assembling the product, for example, the slope portion 361 also helps to smoothly guide the drive shaft 42 and the protective tube 67 which are inserted through the outer tube 32, into the sheath tube 22.

The seal member 64 is disposed in the passage 651 of the outer tube holding portion 65 and is in close contact with the passage 651 and comprises a through-hole 641 at a central portion of the seal member 64. In the illustrated embodiment, the seal member 64 is positioned distally of the distal-most end of the outer tube 32 (outer tube main body 36). The seal member 64 may be embedded in the relay connector 33 or may be fixed to the relay connector 33 by being pinched by the relay connector 33 and the distal portion of the outer tube main body 36. The seal member 64 is deformable in a flexible manner. It is preferable that the through-hole 641 is shut or closed and maintains a sealed state when in a state where nothing is inserted into or positioned in the through-hole 641 of the seal member 64. The through-hole 641 is widened by being pressed by the drive shaft 42 or the protective tube 67, and can receive the drive shaft 42 or the protective tube 67. In this case, for example, the through-hole 641 possesses a slit shape. However, there is no limitation particularly as long as the through-hole 641 is a hole which can be in a sealed state. Since the through-hole 641 (inner surface of the through-hole) of the seal member 64 comes into close contact with the outer circumferential surface of the protective tube 67 in a slidable manner, even though physiological saline solution supplied through the port 311 of the hub 31 passes through the inner tube 34 and the protective tube 67 and flows into the sheath tube 22, the physiological saline solution does not leak into the outer tube 32 from between the relay connector 33 and the protective tube 67. Since the seal member 64 prevents physiological saline solution and blood from leaking, even when the protective tube 67 moves all the way to the proximal side in a state where the female connector 372 (the first connector) provided in the unit connector 37, and the second connector 35 are connected to each other (refer to FIG. 4), the seal member 64 is provided at a position in contact with the outer surface of the protective tube 67. As the material of the seal member 64, for example, natural rubber, silicone rubber, nitrile rubber, fluororubber, or the like can be applied. However, the material of which the seal member 64 is made is not limited to these materials. In addition, the seal member 64 may have a ring seal structure including an O-ring, an X-ring, or the like. In this case, the seal member 64 may be structured to be provided with a hemostatic device such as a Y-connector and the like at a position on the proximal side (for example, the second connector) from the seal member.

Figure 6:
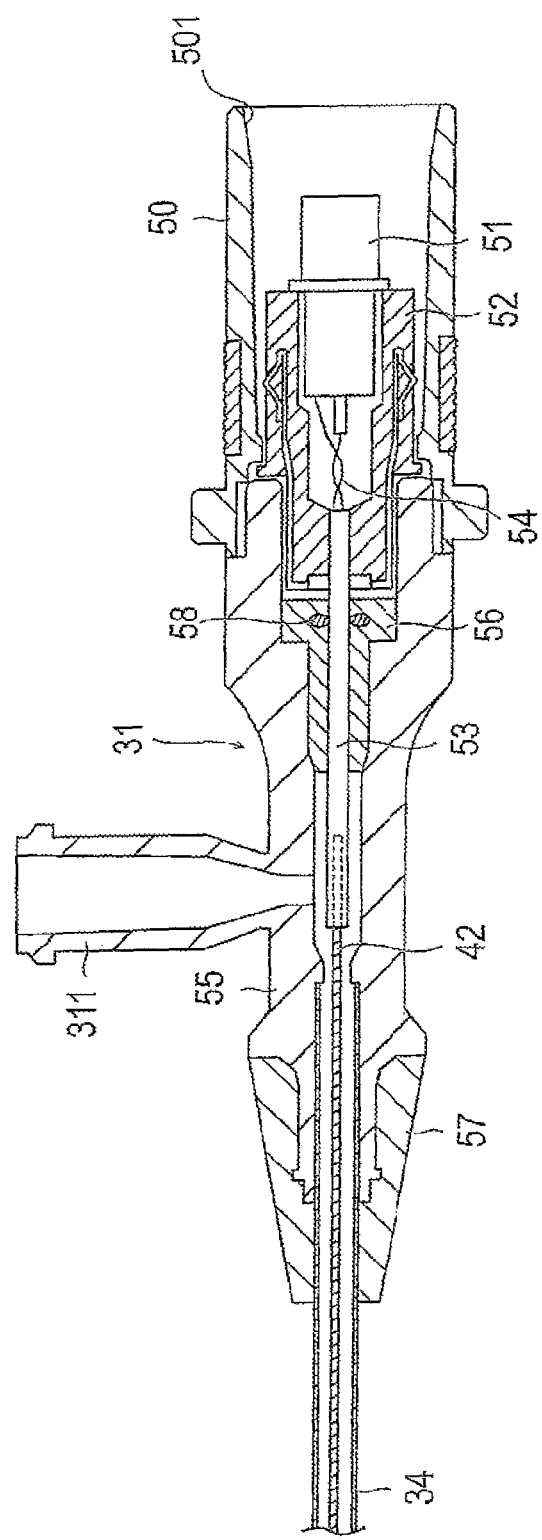
FIG. 6 is a cross-sectional view in the longitudinal direction illustrating a hub of the ultrasound catheter in the first embodiment.

As illustrated in FIG. 6, the hub 31 of the operation unit 3 includes a joint 50, a male connector 51 for driving, a rotor 52, a connection pipe 53, the signal line 54, a hub main body 55, a sealing portion 56, and an anti-kink protector 57.

The joint 50 includes an opening portion 501 provided on the operator's hand-side of the ultrasound catheter 1, and the male connector 51 for driving and the rotor 52 are disposed inside the joint 50. The male connector 51 for driving can be joined to a female connector 711 for driving included in the external drive apparatus 7 (refer to FIG. 2), through the opening portion 501 side of the joint 50. Accordingly, the external drive apparatus 7 and the male connector 51 for driving are mechanically and electrically joined to each other.

The connection pipe 53 is held by the rotor 52 so as not to be able to rotate relative to the connection pipe 53 (i.e., the connection pipe 53 and the rotor 52 are integrated so that movement/rotation of one causes movement/rotation of the other), and the rotor 52 rotates integrally with the male connector 51 for driving. The drive shaft 42 is held by the connection pipe 53 at the end portion of the connection pipe 53 opposite to the rotor 52 in order to transmit rotary motions of the rotor 52 to the drive shaft 42. In addition, the rotor 52 is interposed between the joint 50 and the hub main body 55, and motions of the rotor 52 in the axial direction are restricted. The signal line 54 leads to the inside of the connection pipe 53. One end of the signal line 54 is connected to the male connector 51 for driving, and the other end of the signal line 54 is connected to the transducer unit 41 by passing through the inside of the drive shaft 42. An observation result of the transducer unit 41 is transmitted to the external drive apparatus 7 via the male connector 51 for driving, is subjected to suitable processing, and is displayed as an image.

Physiological saline solution is injected into the hub main body 55 through the port 311, and the physiological saline solution is guided into the inner tube 34 without leaking outside. Since the sealing portion 56 comprising an O-ring 58 is installed between the hub main body 55 and the joint 50, physiological saline solution does not leak onto the opening portion 501 side of the joint 50.

The inner tube 34 is partially fitted into the hub main body 55, and the anti-kink protector 57 is disposed on the outer periphery of the inner tube 34 and the hub main body 55.

As illustrated in FIG. 2, the above-described ultrasound catheter 1 is connected to and driven by the external drive apparatus 7. On a base 75, the external drive apparatus 7 comprises a drive unit 71 which has an external drive source such as a motor and the like built-in so as to rotatively drive the drive shaft, moving means 72 for grasping the drive unit 71 and moving the drive unit 71 in the axial direction by using the motor or the like, and a holding portion 73 which holds a portion of the ultrasound catheter 1 which is fixed at a position. The external drive apparatus 7 is connected to a control unit 79 which controls the drive unit 71 and the moving means 72, and a display portion 78 connected to the control unit 79 displays an image obtained by the transducer unit 41.

The moving means 72 is a feed mechanism which can fixedly grasp the drive unit 71 and moves the fixedly grasped drive unit 71 forward and rearward along a groove rail 76 on the base 75.

The drive unit 71 includes the female connector 711 for driving to which the male connector 51 for driving of the ultrasound catheter 1 can be connected, and a joint connection portion 712 which can be connected to the joint 50 of the ultrasound catheter 1. As a result of the connection, the drive unit 71 can transmit and receive a signal with respect to the transducer unit 41 and can rotate the drive shaft 42 at the same time.

Ultrasound which is transmitted and received by the ultrasound transducer 411 provided in the housing 412 is scanned in a substantially radial direction by transmitting rotary motions of the motor inside the drive unit 71 to the drive shaft 42 and rotating the housing 412 fixed to the distal end of the drive shaft 42, thereby performing ultrasound scanning of the ultrasound catheter 1. In addition, as the ultrasound catheter 1 in its entirety is pulled to the proximal side or in the proximal direction, and the ultrasound transducer 411 is moved in a longitudinal direction, a 360-degree tomographic image of a surrounding tissue to an arbitrary position inside a blood vessel throughout the axial direction can be obtained by performing scanning.

Subsequently, descriptions will be given regarding an operation when observing the inside of a lumen by applying the ultrasound catheter 1 in the first embodiment.

First, a priming operation of filling the inside of the ultrasound catheter 1 with physiological saline solution is performed before the sheath 2 of the ultrasound catheter 1 is inserted into a lumen. Air inside the ultrasound catheter 1 is removed and air is prevented from entering the inside of a lumen such as a blood vessel and the like by performing the priming operation.

In order to perform priming, the male connector 352 of the second connector 35 is caused to be in a state of being connected to the female connector 372 of the unit connector 37 in a liquid-tight manner, the hub 31 is pulled to the fullest extent to the operator's hand-side, that is, in a state where the inner tube 34 is drawn out to the fullest extent from the outer tube 32 (refer to FIG. 4), and physiological saline solution is injected, for example, by applying an injector or the like via an instrument configured to include a tube, a three-way stopcock, an injector, and the like which are connected to the port 311 of the hub 31. The injected physiological saline solution sequentially passes through the hub 31, the inner tube 34, and the protective tube 67 and fills the inside of the sheath 2. Since the space between the relay connector 33 and the protective tube 67 is sealed by the seal member 64, the physiological saline solution does not leak into the outer tube 32 from between the relay connector 33 and the protective tube 67.

When the inside of the ultrasound catheter 1 is completely filled with the physiological saline solution, the physiological saline solution comes out or is discharged through the priming lumen 231 which is formed in the filling liquid inflow and outflow path member 23 (refer to FIG. 3) of the sheath 2. In this manner, a filling state of the physiological saline solution is confirmed. It is possible to remove air inside the ultrasound catheter 1 and to prevent air from entering the inside of a lumen by performing the priming operation.

Subsequently, as illustrated in FIG. 2, the ultrasound catheter 1 is joined to the external drive apparatus 7 which is covered with a sterilized bag or the like made of polyethylene. In other words, the joint 50 (refer to FIG. 6) of the hub 31 of the ultrasound catheter 1 is connected to the joint connection portion 712 of the drive unit 71. In this manner, a signal can be transmitted and received between the transducer unit 41 and the external drive apparatus 7, and the drive shaft 42 can be rotated at the same time. Then, as the unit connector 37 fits the holding portion 73, joining processing is completed.

Subsequently, the hub 31 is thrust or moved in the distal direction by moving the drive unit 71 in the distal direction along the groove rail 76 on the base 75 so as to cause the inner tube 34 to be in a state of being thrust or inserted into the outer tube 32 all the way to the end (refer to FIG. 1). In the aforementioned state, the sheath 2 is inserted into a human body, and the insertion stops when the distal end of the sheath 2 passes over a target lesion.

Figure 7:
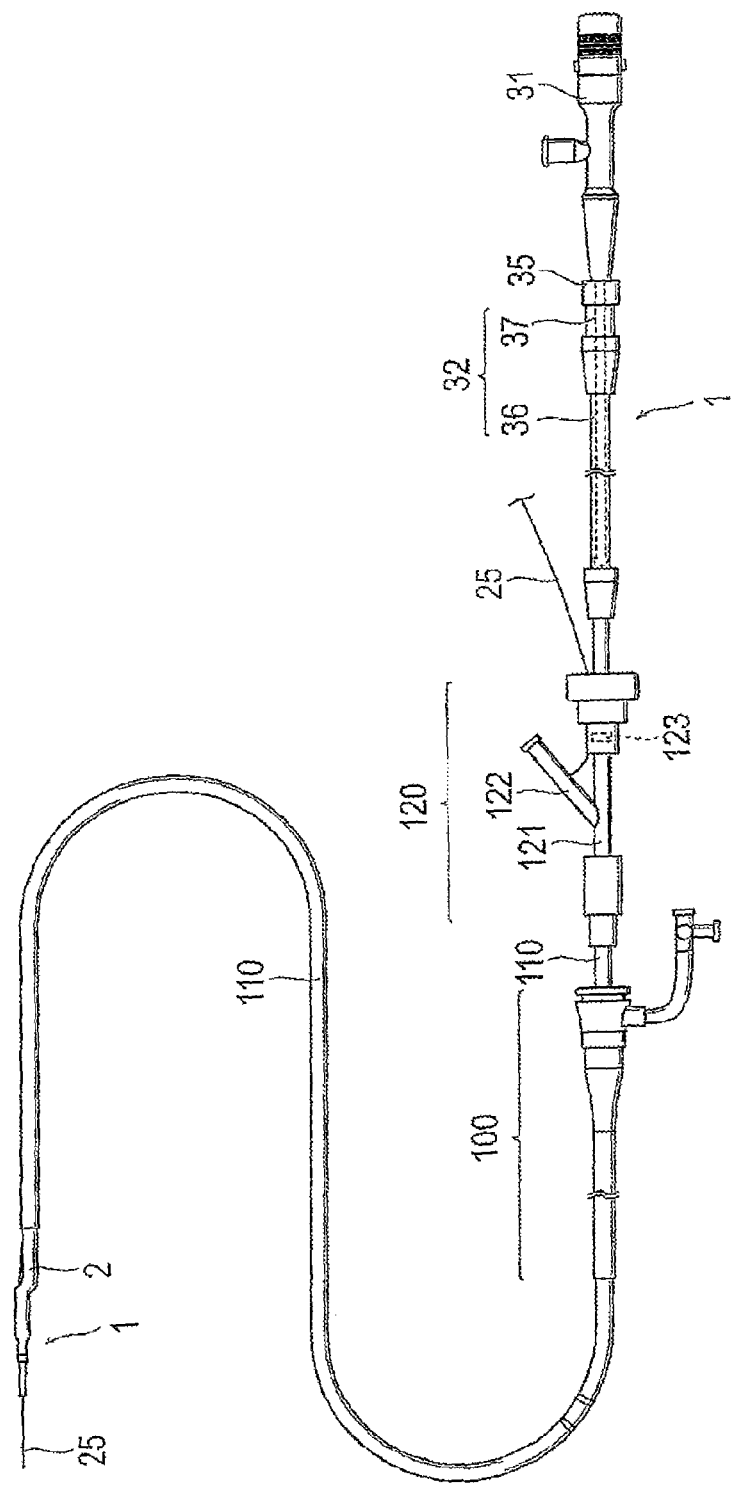
FIG. 7 is a plan view illustrating a state where the ultrasound catheter in the first embodiment is inserted into a lumen.

As an example, as illustrated in FIG. 7, to insert the ultrasound catheter 1 into a blood vessel of the coronary artery of the heart, an introducer sheath 100 is first caused to be indwelled in the femoral artery or the like through the Seldinger's method or the like before the ultrasound catheter 1 is inserted. Then, a guiding catheter 110 is inserted into a human body via the introducer sheath 100, and the guiding catheter 110 is indwelled at the entrance of the blood vessel of the coronary artery.

Thereafter, the guide wire 25 is inserted into the blood vessel of the coronary artery to a target place, passing through the guiding catheter 110. Then, while the guide wire 25 which is inserted into the blood vessel passes through the guide wire lumen 211 of the ultrasound catheter 1, the sheath 2 of the ultrasound catheter 1 is inserted into the human body through the guiding catheter 110.

A Y-shaped Y-connector 120 including a main body portion 121 which coaxially communicates with the guiding catheter 110 and a side port 122 which is branched off from the main body portion 121 is joined to the proximal end of the guiding catheter 110. Sealing efficiency of a clearance portion between the ultrasound catheter 1 and the guiding catheter 110 is ensured on account of the Y-connector 120.

The ultrasound catheter 1 is inserted into the lumen through a valve body 123 of the Y-connector 120 which is connected to the guiding catheter 110 on the proximal side, and the insertion speed of being inserted into the lumen is slowed down at the timing when the marking portion M approaches the vicinity of the valve body 123. The ultrasound catheter 1 is inserted along the guide wire 25 to a target lesion to be observed.

Subsequently, after the ultrasound catheter 1 arrives at the target site inside the lumen of the living body, the position of the sheath 2 is fixed. In this state, a pull-back operation is performed while the drive shaft 42 is rotated by the drive unit 71 so that images of the lumen in the axial direction are acquired.

The pull-back operation can be performed by causing the control unit 79 to operate the moving means 72 which is connected to the rear end portion of the ultrasound catheter 1. The acquired data is subjected to digital processing performed by the control unit 79, and then, the display portion 78 displays the data as image data.

Then, after the pull-back operation, the hub 31 is thrust into or moved in the distal direction again, and the imaging core 4 is caused to move forward. Thereafter, the ultrasound catheter 1 is operated to be pulled out of the inside of the lumen. However, for example, when the ultrasound catheter 1 has been inserted into a curved lumen, since the ultrasound catheter 1 has the rapid-exchange structure, there is a possibility of an occurrence of a phenomenon, that is, so-called "wire separation" in which the guide wire 25 is warped and is separated from the ultrasound catheter 1 as the ultrasound catheter 1 is pulled in the proximal direction. When such a phenomenon occurs and the guide wire 25 is bent so as to turn back, for example, there is a concern that the ultrasound catheter 1 is unlikely to move along the guide wire 25. In addition, in a case where the ultrasound catheter 1 is used, for example, to confirm a stent which indwells inside the lumen, there is a concern that the ultrasound catheter 1 or the guide wire 25 is caught by a strut of the stent and the ultrasound catheter 1 may be difficult to pull out.

Figure 8:
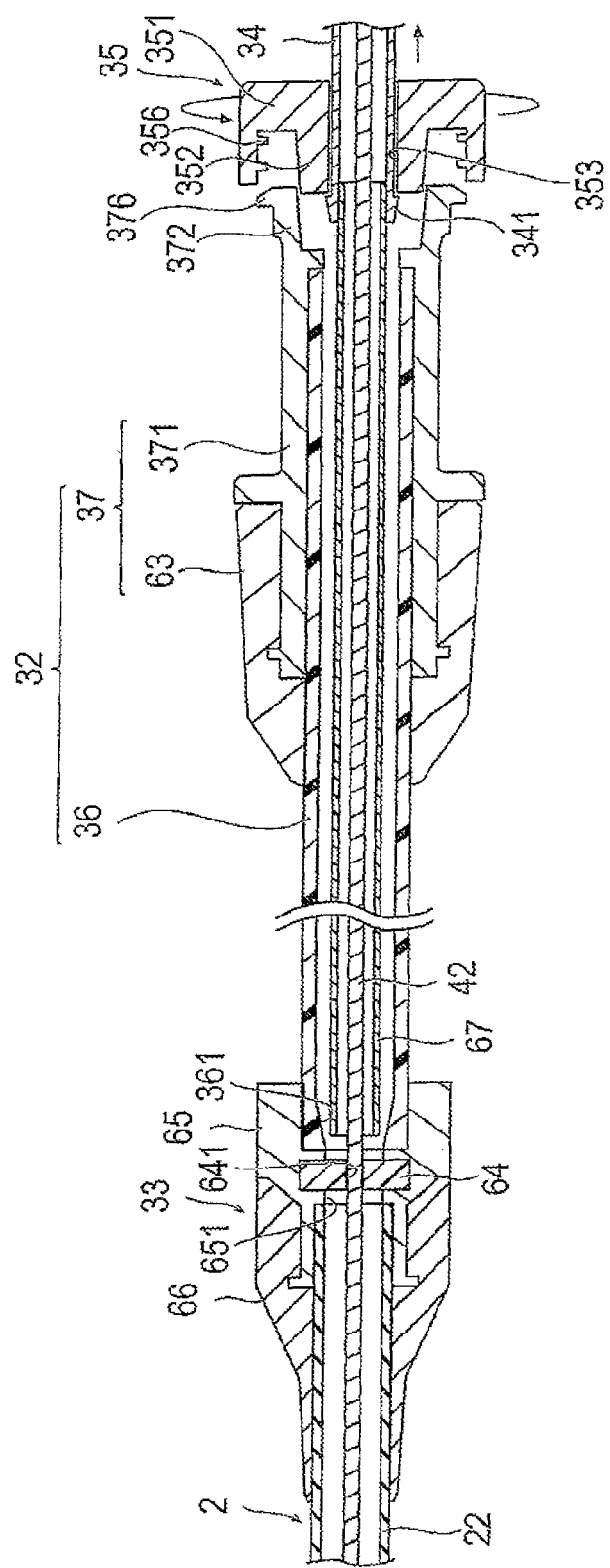
FIG. 8 is a cross-sectional view in the longitudinal direction illustrating a state where a second connector is disconnected.
Figure 9:
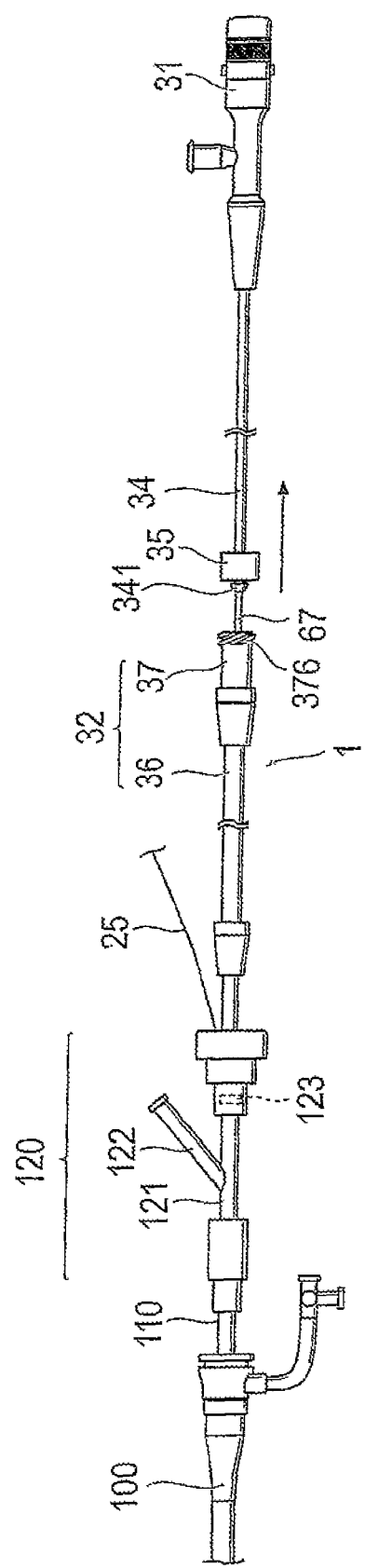
FIG. 9 is a plan view illustrating a state where the second connector is disconnected.
Figure 10:
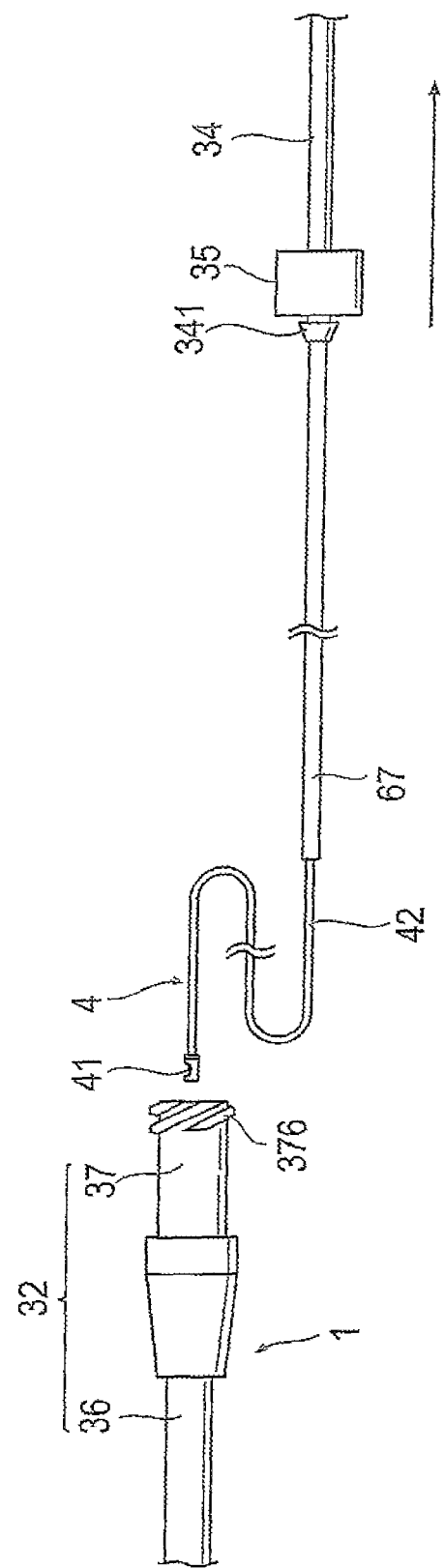
FIG. 10 is a plan view illustrating a state where an imaging core is pulled out of a sheath.

In such a case, an operator separates the male screw portion 376 from the female screw portion 356 by rotating the second connector 35 of the ultrasound catheter 1, and thus, the male connector 352 provided in the second connector 35 is disconnected from the female connector 372 provided in the unit connector 37. Then, when the hub 31 in the entirety of the external drive apparatus 7 is moved to the proximal side (in the proximal direction) while in a state where the outer tube 32 is grasped and fixed, the inner tube 34, the protective tube 67, the imaging core 4, and the second connector 35 move to the proximal side (in the proximal direction) together with the hub 31 as illustrated in FIGS. 8 and 9. When the hub 31 is moved to the proximal side (in the proximal direction) further, the protective tube 67 and the imaging core 4 are pulled out of the sheath 2 and the outer tube 32 as illustrated in FIG. 10.

Figure 11:
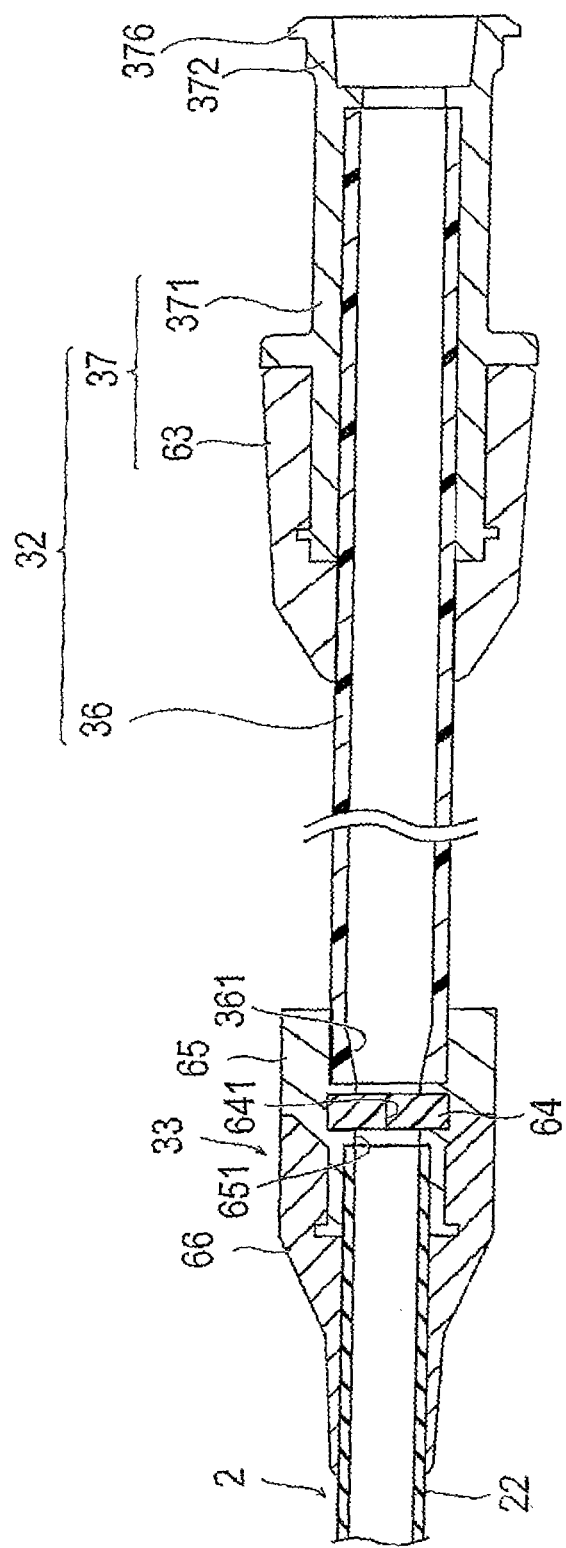
FIG. 11 is a cross-sectional view in the longitudinal direction illustrating a state where the imaging core is pulled out of the sheath.

Then, when the protective tube 67 and the imaging core 4 are completely pulled out of the sheath 2 and the outer tube 32, the through-hole 641 in the seal member 64 is shut or automatically closes (self-closes) as illustrated in FIG. 11. Accordingly, the seal member 64 prevents blood from leaking via the lumen of the sheath 2, thereby improving the safety, and blood does not leak on the hand-side of an operator, thereby improving the operability as well.

Figure 12:
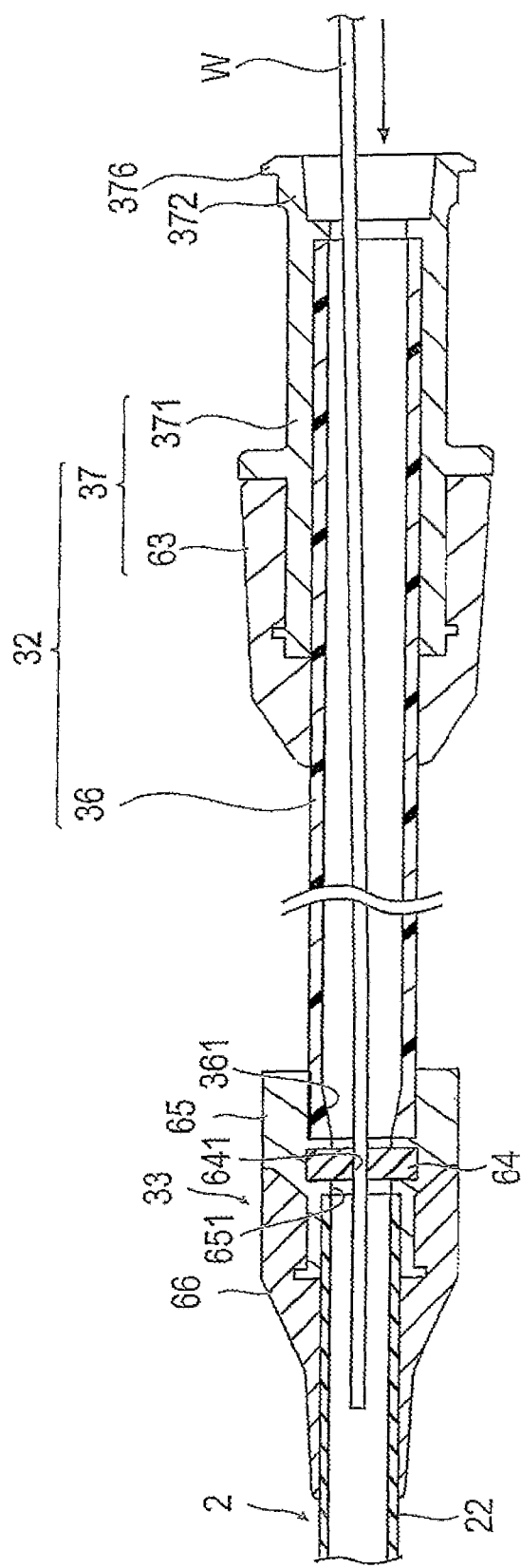
FIG. 12 is a cross-sectional view in the longitudinal direction illustrating a state where a wire is inserted through an outer tube after the imaging core is pulled out of the sheath.

Thereafter, as illustrated in FIG. 12, a wire W which is a separately prepared guide wire or the like is inserted into the lumen in which the imaging core 4 was disposed. In this case, since the tapered slope portion 361 is formed on the inner circumferential surface at the distal end portion of the outer tube main body 36 and the inner diameter of the distal end of the slope portion 361 is substantially the same as the inner diameter of the passage 651, the wire W which is inserted through the outer tube 32 can be smoothly inserted or led into the sheath tube 22. In other words, it is possible to relatively easily introduce the wire W into the sheath tube 22 by utilizing the outer tube main body 36 which has an inner diameter greater than the inner diameter of the sheath tube 22. Then, the seal member 64 allows the wire W to be inserted therethrough and prevents blood from leaking via the lumen of the sheath 2.

After the wire W is caused to arrive at the distal portion of the sheath 2, force is applied to the inside of the sheath 2 using the wire W, and the sheath 2 and the guide wire 25 are operated. Thus, the sheath 2 and the guide wire 25 can return to an appropriate state. Accordingly, the sheath 2 and the guide wire 25 can be pulled out of the lumen.

As described above, in the ultrasound catheter 1 according to the first embodiment, the outer tube 32 which includes the female connector 372 (the first connector) is provided on the proximal side of the sheath 2 on the proximal side. The second connector 35 which can be connected to and disconnected from the female connector 372 is provided in the outer tube 32 on the proximal side. The inner tube 34 which moves relatively to the outer tube 32 inside the outer tube 32 in accordance with a movement of the hub 31 is provided. The stopper 341 (the engagement portion) which cannot pass through the inner side of the second connector 35 is provided in the distal portion of the inner tube 34. Therefore, in a state where the second connector 35 is connected to the outer tube 32, the inner tube 34 can be held so as not to come out due to the stopper 341 caught by the second connector 35. Furthermore, the second connector 35 is disconnected from the outer tube 32, and the hub 31 is moved to the proximal side. Thus, the imaging core 4 can be pulled out of the sheath 2.

Then, the ultrasound catheter 1 is provided with the protective tube 67 which protrudes toward the distal side further than the inner tube 34, accommodates the drive shaft 42, can be inserted into the outer tube 32 and the sheath 2, and is pulled out of the outer tube 32 together with the hub 31 and the inner tube 34 as the second connector 35 is disconnected from the female connector 372 (the first connector). Therefore, when the inner tube 34 is thrust into or drawn out of the outer tube 32, the drive shaft 42 can be prevented from bending or the like by the protective tube 67, and when the imaging core 4 is pulled out of the sheath 2, the protective tube 67 is pulled out together with the hub 31 and the inner tube 34. Therefore, when the wire W is inserted into the lumen in which the imaging core 4 was disposed, there is no need to insert the wire W through the protective tube 67, thereby improving the operability. In addition, since the thin protective tube 67 does not protrude from the outer tube 32 side through which the wire W is inserted, the safety is improved when the wire W is inserted therethrough.

In addition, in the ultrasound catheter 1 in the first embodiment, the second connector 35 is provided in the outer tube 32 on the proximal side instead of the distal side and is disposed being away from the Y-connector 120 during the operation. Therefore, the second connector 35 does not interfere with the guide wire 25 which has led from the Y-connector 120, and the guide wire 25 is relatively easily controlled even when the ultrasound catheter 1 is operated, thereby improving the operability of the guide wire 25 and the ultrasound catheter 1.

In addition, since the relay connector 33 (the sheath connection portion) comes into contact with the outer circumferential surface of the protective tube 67 in a slidable manner, and there is provided the seal member 64 that shuts or closes the passage 651 through which the protective tube 67 is inserted as the protective tube 67 and the imaging core 4 are pulled out, when the protective tube 67 and the imaging core 4 are completely pulled out, the through-hole 641 of the seal member 64 is shut or closed and is in a sealed state as illustrated in FIG. 11. Moreover, since the outer tube 32 is provided in the relay connector 33 on the proximal side on which the seal member 64 is provided, blood leaking from the seal member 64 does not reach the outside unless the blood passes through the outer tube 32 further. Therefore, blood is prevented from leaking via the lumen of the sheath 2, thereby improving the safety, and blood does not leak on the hand-side of an operator, thereby improving the operability as well.

In addition, since the protective tube 67 is fixed to the inner tube 34, the protective tube 67 is moved in accordance with (together with) a movement of the inner tube 34.

In addition, since the protective tube 67 is the tubular body which is impermeable to liquid, blood, physiological saline solution, or the like circulating inside the protective tube 67 does not leak into the outer tube 32 via the protective tube 67. As a result, since there is no need to inject priming liquid such as physiological saline solution and the like into a portion of the outer tube, it is possible to improve the operability, and since air remaining inside the protective tube 67 can be reduced, it is possible to shorten the preparation time when in use. In addition, since blood, physiological saline solution, or the like does not leak into the outer tube 32, there is no need to provide the seal member between the outer tube 32 and the inner tube 34. Then, since liquid such as blood, physiological saline solution, and the like is prevented from leaking into the outer tube 32, the liquid is more reliably prevented from leaking out further than the outer tube 32, and since the liquid does not leak on the hand-side of an operator, thereby improving the operability as well.

In addition, since the slope portion 361 which slopes toward the axial center in the distal direction is formed on the inner circumferential surface of the outer tube 32, the wire W, the imaging core 4, the protective tube 67, and the like which are inserted through the outer tube 32 can be smoothly guided into the sheath tube 22 of which the inner diameter is smaller than the outer tube 32.

In addition, since the ultrasound catheter 1 in the first embodiment is disconnected by the second connector 35, it is possible for the sheath 2 and the outer tube 32 side which is inserted into the lumen and is able to be manufactured at lower costs to be disposable, and it is possible to cause the hub 31 and the inner tube 34 side comprising the imaging core 4 which are more expensive to be reusable. In addition, in the ultrasound catheter 1 according to the present embodiment, since the sheath 2 side can be disconnected by the second connector 35, it is possible to replace the sheath with another one which is different in thickness, length of the monorail, and the like, for example, in accordance with the usage condition of the ultrasound catheter 1.

Figure 13:
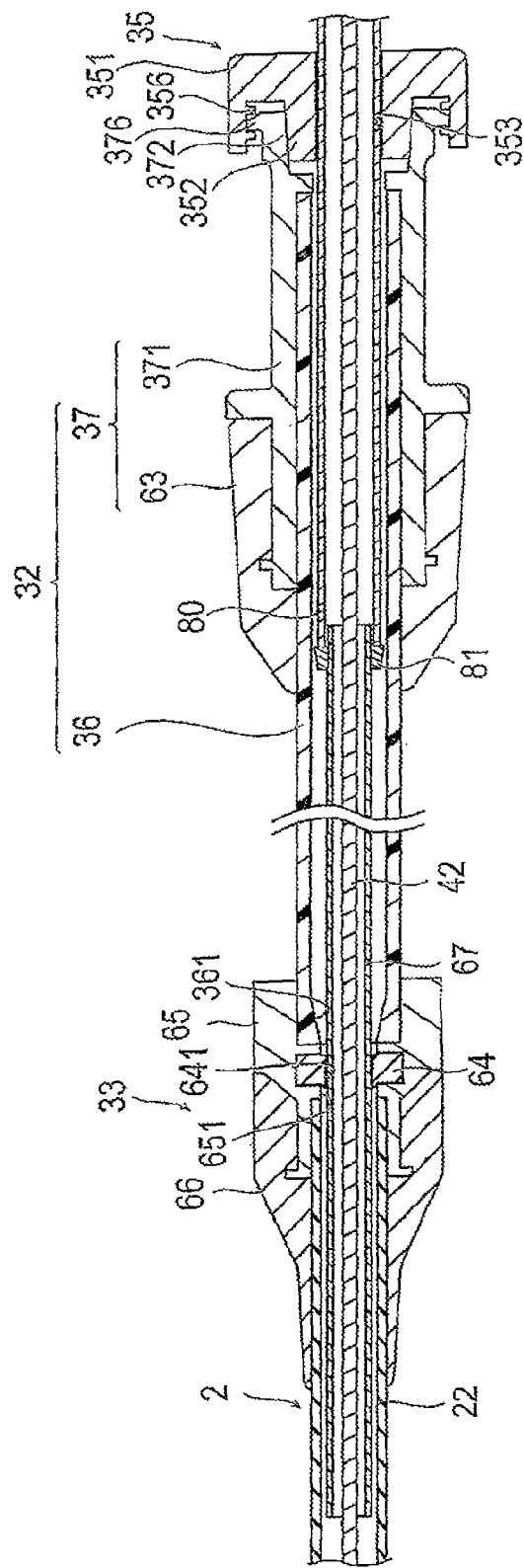
FIG. 13 is a cross-sectional view in the longitudinal direction illustrating a modification example of an engagement portion of the ultrasound catheter in the first embodiment.

The stopper 341 (the engagement portion) of the ultrasound catheter 1 in the first embodiment is at the distal portion of the inner tube 34 and is formed as a portion of the inner tube 34. However, the engagement portion does not need to be formed as a portion of the inner tube. For example, as described in a modification example of the ultrasound catheter in the first embodiment illustrated in FIG. 13, an engagement portion 81 formed with a member which is different from the inner tube 80 and the protective tube 67 (i.e., an engagement portion 81 formed with a member that is neither part of the inner tube 80 nor part of the protective tube 67) may be provided at the distal portion of an inner tube 80. Even in such a configuration, the engagement portion 81 can be prohibited from passing through the inner side of the second connector 35, and in a state where the second connector 35 is connected to the outer tube 32, the inner tube 80 is held so as not to come out due to the engagement portion 81 being caught by the second connector 35.

Figure 14:
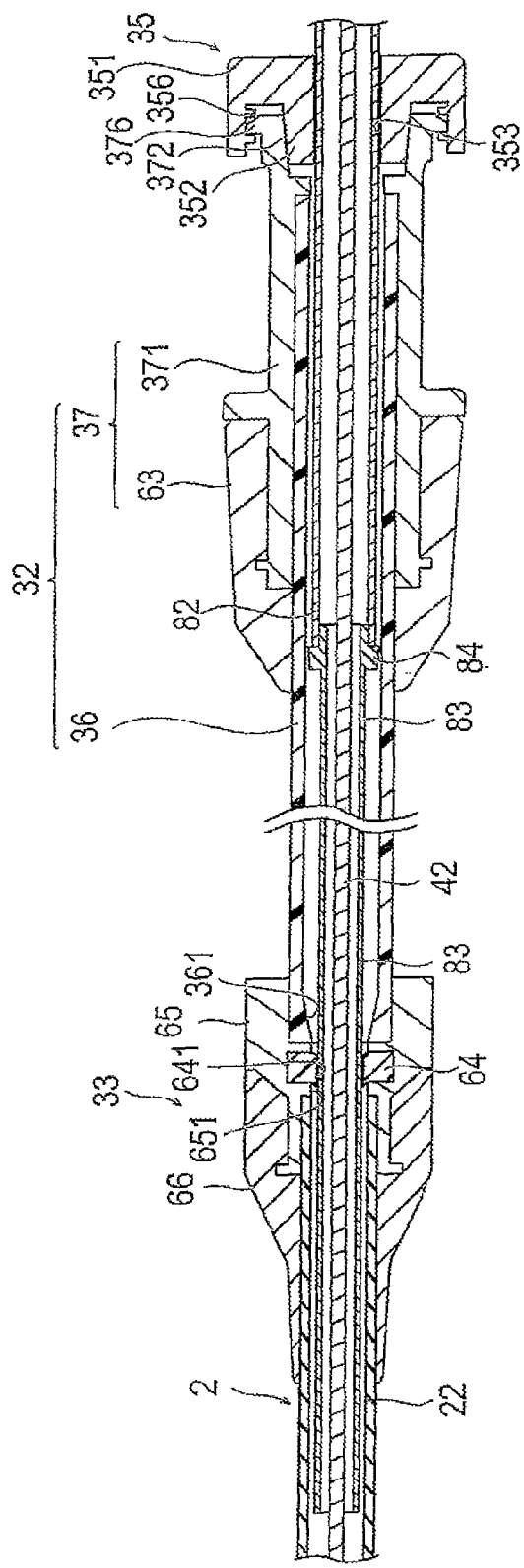
FIG. 14 is a cross-sectional view in the longitudinal direction illustrating an alternative modification example of the engagement portion of the ultrasound catheter in the first embodiment.

In addition, as described in an alternative modification example of the ultrasound catheter in the first embodiment illustrated in FIG. 14, an engagement portion 84 may be formed as a portion (enlarged portion) of a protective tube 83 instead of the inner tube 82. With such a configuration, the engagement portion 84 is prohibited from passing through the inner side of the second connector 35.

Figure 15:
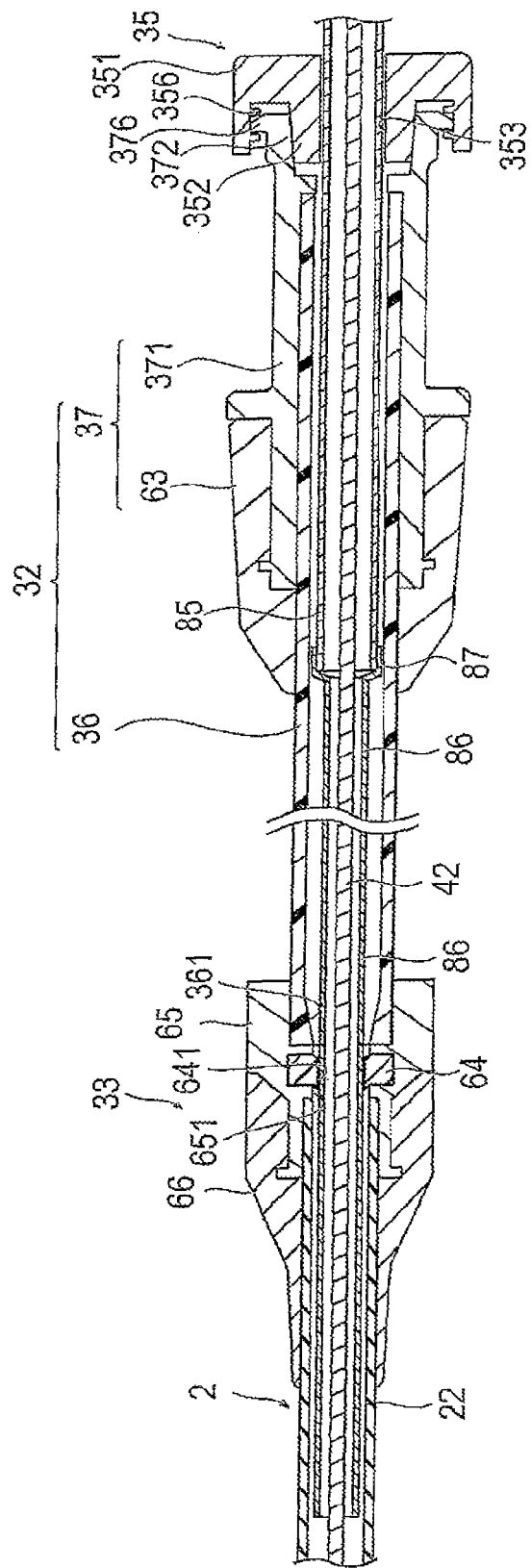
FIG. 15 is a cross-sectional view in the longitudinal direction illustrating another alternative modification example of the engagement portion of the ultrasound catheter in the first embodiment.

In addition, as described in another alternative modification example of the ultrasound catheter in the first embodiment illustrated in FIG. 15, an engagement portion 87 may be formed as a portion of the protective tube 86 covering the inner tube 85. Thus, in this embodiment, the proximal end portion of the protective tube 86 axially overlaps and covers the outer peripheral surface of a distal portion of the inner tube 85. With such a configuration, the engagement portion 87 can be prohibited from passing through the inner side of the second connector 35.

Figure 16:
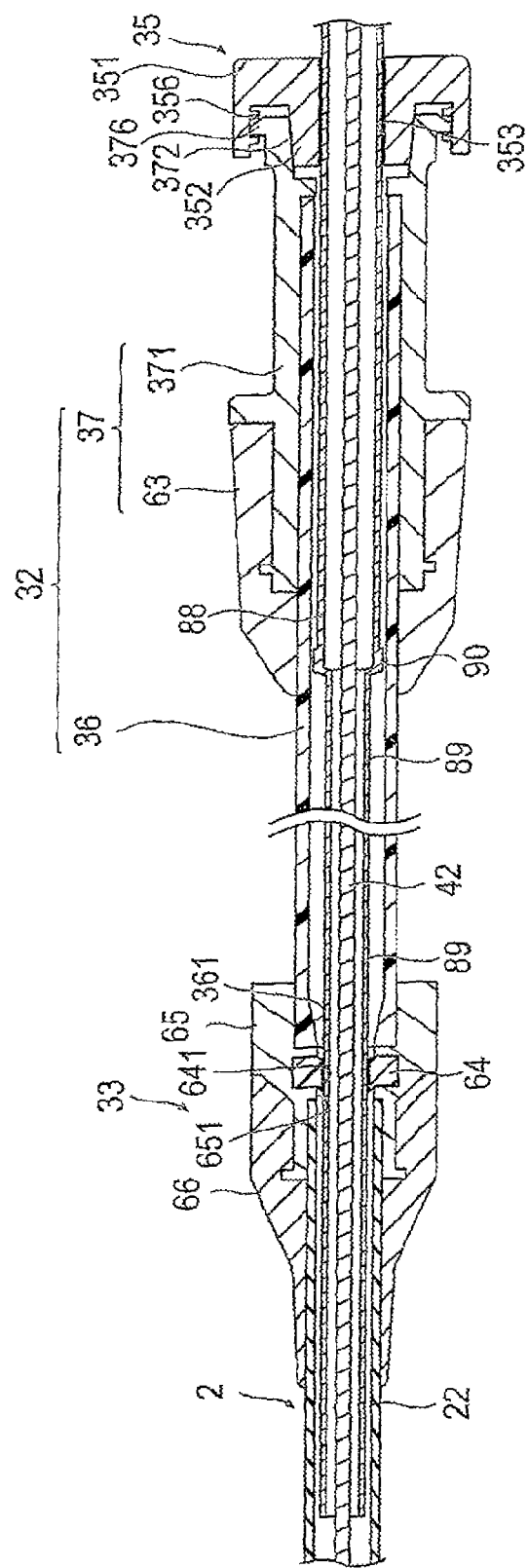
FIG. 16 is a cross-sectional view in the longitudinal direction illustrating further another alternative modification example of the engagement portion of the ultrasound catheter in the first embodiment.

In addition, as described in further another alternative modification example of the ultrasound catheter in the first embodiment illustrated in FIG. 16, the inner tube 88, the protective tube 89, and the engagement portion 90 may be integrally formed as the same member. Even in such a configuration, the engagement portion 90 can be prohibited from passing through the inner side of the second connector 35.

Figure 17:
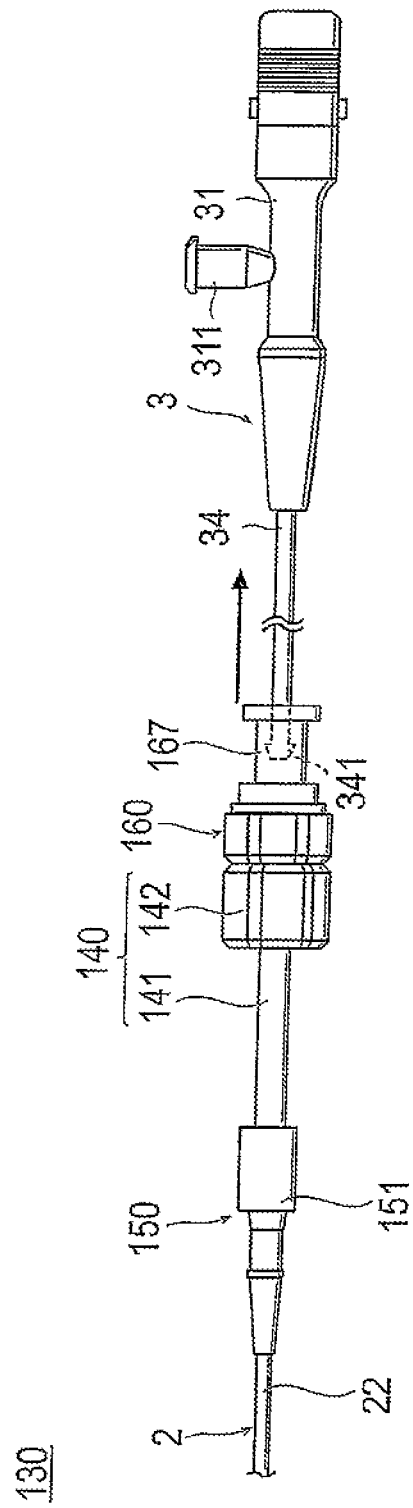
FIG. 17 is a plan view illustrating an operation unit of an ultrasound catheter in a second embodiment.
Figure 18:
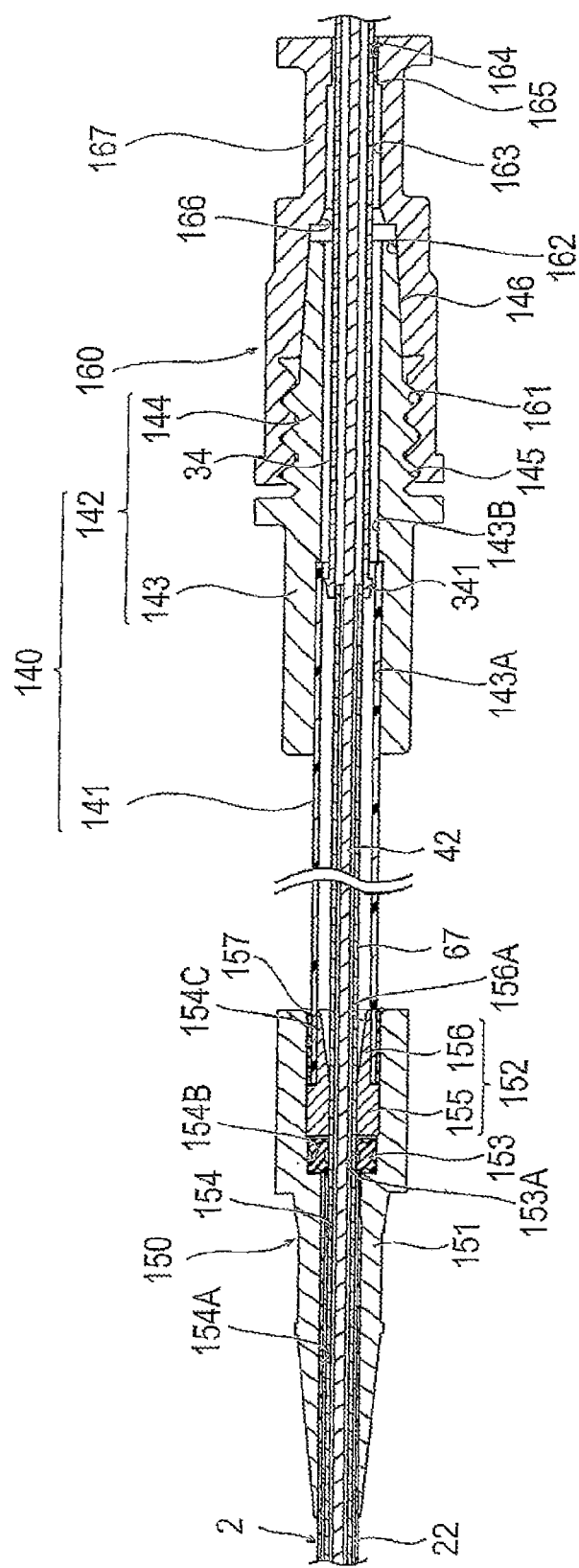
FIG. 18 is a cross-sectional view in the longitudinal direction illustrating a unit connector and a relay connector of the ultrasound catheter in the second embodiment.

As illustrated in FIGS. 17 and 18, an ultrasound catheter 130 according to a second embodiment, representing another example of the inventive catheter disclosed here, differs from the ultrasound catheter 1 in the first embodiment in the configurations of an outer tube 140 which is provided in the sheath 2 on the proximal side, a relay connector 150 (the sheath connection portion) which connects the outer tube 140 and the sheath 2 to each other, and a unit connector proximal portion 160 (the second connector) which is configured to be connected to and disconnected from the outer tube 140 on the proximal side. third The outer tube 140 comprises an outer tube main body 141 of which the distal portion is connected to the relay connector 150, and a substantially tubular unit connector distal portion 142 to which a proximal portion of the outer tube main body 141 is fixed. The outer tube main body 141 is formed with a tubular body of which the inner diameter and the outer diameter are uniform along an axial line direction.

The unit connector distal portion 142 comprises an outer tube fixing portion 143 to which the outer tube main body 141 is fixed, and a first connector 144 to which the unit connector proximal portion 160 is connected. The first connector 144 comprises a male screw portion 145 on the outer circumferential surface of the first connector 144, and a tapered male connector 146. The male connector 146 is formed on the proximal side from the male screw portion 145. The male screw portion 145 is formed in a shape of a trapezoid-threaded screw in which the apex portions of a screw thread are cut to be flat and a cross-section thereof exhibits a trapezoid. The pitch of the screw thread in the male screw portion 145 is 2 mm. However, the pitch is not limited to this pitch. The male screw portion 145 is formed to have one screw thread. However, the male screw portion 145 may be formed to have two or more screw threads.

An outer tube accommodation portion 143A in which the outer tube main body 141 fixedly fits is formed on the inner circumferential surface of the outer tube fixing portion 143, and a first inner diameter portion 143B having the inner diameter which is greater than the inner diameter of the outer tube main body 141 and smaller than the outer diameter of the outer tube main body 141 is formed in the outer tube accommodation portion 143A on the proximal side. The inner tube 34 is movable together with the stopper 341 inside the first inner diameter portion 143B and the outer tube main body 141.

The unit connector proximal portion 160 (the second connector) possesses a substantially tubular shape. A female screw portion 161, a tapered female connector 162 which is configured to be connected to the male connector 146 of the unit connector 37 and to be disconnected from the male connector 146, a second inner diameter portion 163 of which the inner diameter is smaller than the inner diameter of the female connector 162 and greater than the outer diameter of the stopper 341, and a pass-through port 164 of which the inner diameter is smaller than the outer diameter of the stopper 341 are provided on the inner circumferential surface of the unit connector proximal portion 160 on the distal side. The female connector 162 is formed on the proximal side from the female screw portion 161. The second inner diameter portion 163 is on the proximal side from the female connector 162, and the pass-through port 164 is on the proximal side from the second inner diameter portion 163. A step difference portion 165 of which the inner diameter varies is formed between the second inner diameter portion 163 and the pass-through port 164.

Since the pass-through port 164 has an inner diameter smaller than the outer diameter of the stopper 341, the stopper 341 cannot pass through the pass-through port 164. A guidance portion 166 of which the inner diameter is widened in a tapered manner toward the distal end or in a distal direction is formed in the second inner diameter portion 163 on the distal side. When the stopper 341 moves inside the unit connector proximal portion 160 in the proximal direction, the guidance portion 166 prevents the stopper 341 from being caught and facilitates smooth movement of the stopper 341.

A clamp portion 167 which is held (clamped) by the holding portion 73 (refer to FIG. 2) of the external drive apparatus 7 is formed on the outer circumferential surface of the unit connector proximal portion 160 on the proximal side.

The female connector 162 and the male connector 146 comprise a luer taper structure in which a predetermined gradient is formed so as to exhibit high fitting force. The unit connector distal portion 142 and the unit connector proximal portion 160 are fixed to each other on account of friction force generated by screwing the male screw portion 145 of the unit connector distal portion 142 into the female screw portion 161 of the unit connector proximal portion 160, and thus, a state where the male connector 146 is connected with the female connector 162 can be firmly maintained. The gradient of the female connector 162 and the male connector 146 can be set to 6/100 which is defined by the ISO standard while expecting strong fitting force (friction force) utilizing a wedge effect. However, the gradient is not limited to the gradient mentioned above as long as a wedge effect can be utilized.

Then, since the male screw portion 145 is the trapezoid-threaded screw, when the tapered male connector 146 and the female connector 162 are caused to fit as wedges, it is possible to achieve sufficient strength. In addition, since the male screw portion 145 is the trapezoid-threaded screw, the outer diameter of the male screw portion 145 can be decreased, and the outer diameter of the unit connector proximal portion 160 in which the female screw portion 161 is formed can be decreased. Therefore, when a force acts on the outer circumferential surface of the unit connector distal portion 142 or the unit connector proximal portion 160, and a force acts in a direction in which the unit connector distal portion 142 and the unit connector proximal portion 160 are loosened, it is possible to minimize torque generated with respect to the same acting force and to be prevented from being erroneously detached. In addition, since the male screw portion 145 is the trapezoid-threaded screw, the pitch of the screw thread becomes wide, and the male screw portion 145 can be disconnected from the female screw portion 161 by the small number of rotations, thereby improving working properties. Moreover, it is possible to perform prompt measures, for example, in case of emergency such as an occurrence of "trapping" described below.

In addition, according to the present embodiment, the male screw portion 145 is formed to have one screw thread. However, if the male screw portion 145 is formed to have two or more screw threads, the male screw portion 145 can be disconnected from the female screw portion 161 by the small number of rotations, and thus, it is possible to improve working properties.

In addition, since the male screw portion 145 is the trapezoid-threaded screw, a lead angle becomes less than a contact angle. Therefore, it is possible to expect a high locking effect by utilizing self-locking performance exhibiting high fixing power.

In addition, since the inner tube 34 extending from the hub 31 includes the stopper 341 (the engagement portion) which is at the distal end of the inner tube 34, even when the hub 31 is pulled to the fullest extent, that is, even when the inner tube 34 is drawn out to the fullest extent from the outer tube 140, the stopper 341 is caught by the step difference portion 165 of the unit connector proximal portion 160, and thus, the inner tube 34 can be prevented from slipping out of the unit connector proximal portion 160.

The relay connector 150 includes a substantially tubular outer tube holding portion 151 which holds the outer tube, a spacer 152 which is disposed inside the outer tube holding portion 151, and a seal member 153 (seal). A passage 154 which guides the drive shaft 42 and the protective tube 67 into the sheath tube 22 from the outer tube 140 is located inside the outer tube holding portion 151. The passage 154 is configured to have a sheath accommodation portion 154A to which the sheath tube 22 is fixed, a seal member accommodation portion 154B which accommodates the seal member 153, and a spacer accommodation portion 154C which accommodates the spacer 152. The sheath accommodation portion 154A, the seal member accommodation portion 154B, and the spacer accommodation portion 154C are disposed side by side in the proximal end direction from the distal side. The seal member accommodation portion 154B possesses an inner diameter greater than that of the sheath accommodation portion 154A, and the spacer accommodation portion 154C possesses an inner diameter greater than that of the seal member accommodation portion 154B.

The spacer 152 is a member which is disposed between the outer tube holding portion 151 and the outer tube main body 141. The spacer 152 comprises a tubular spacer distal portion 155 which is fixed to the outer tube holding portion 151, and a spacer proximal portion 156 which is disposed in the spacer distal portion 155 on the proximal side and of which the outer circumferential surface is covered by the outer tube main body 141. The spacer proximal portion 156 of which the outer circumferential surface is covered by the outer tube main body 141 is joined to the outer tube main body 141, and a slope portion 156A which is continuously connected to the inner circumferential surface of the spacer distal portion 155 and of which the inner diameter widens (increases) in the proximal end direction in a tapering manner is formed on the inner circumferential surface of the spacer distal portion 155. The inner circumferential surface of the spacer distal portion 155 helps to position (axially align) the protective tube 67 at the center of the relay connector 150, and the outer circumferential surface of the spacer proximal portion 156 helps to position (axially align) the outer tube main body 141 at the center of the relay connector 150. Outside the outer tube main body 141 which covers the spacer 152, a space is formed with the spacer accommodation portion 154C, and the space is uniformly filled with an adhesive 157.

The slope portion 156A of the spacer proximal portion 156 helps to smoothly guide a guide wire or the like, which is inserted through the outer tube 140, into the sheath tube 22. In addition, when assembling the product, for example, the slope portion 156A also helps to smoothly guide the drive shaft 42 and the protective tube 67, which are inserted through the outer tube 140, into the sheath tube 22. Moreover, the spacer 152 is formed to have the end surface on the distal side wider than the end surface of the outer tube main body 141 on the distal side. That is, the outer dimension of the distal end of the spacer 52 is greater than the outer dimension of the distal end of the outer tube main body 141. Therefore, the spacer 152 helps to hold the seal member 153 and helps maintain favorable sealing efficiency of the seal member 153 by preventing the seal member 153 from jumping out in the proximal end direction. Particularly, when there is provided no spacer 152, there is a possibility that the outer tube main body 141 comes into contact with the seal member 153. As the thin outer tube main body 141 comes into contact with the seal member 153, the seal member 153 is likely to be deformed. However, deformation of the seal member 153 is prevented by providing the spacer 152, and thus, it is possible to maintain favorable sealing efficiency. In the first embodiment, the slope portion 361 is formed on the inner side surface of the outer tube main body 36. However, as the spacer 152 in which the slope portion 156A is formed as in the second embodiment is provided as a member separated from the outer tube main body 141, even when the outer tube main body is relatively thin and it is difficult to form a slope portion in the outer tube main body itself, the slope portion 156A can be relatively easily formed by utilizing the spacer 152.

The seal member 153 is the ring seal structure including the O-ring, the X-ring, or the like. The seal member 153 is disposed in close contact with the seal member accommodation portion 154B of the outer tube holding portion 151 and comprises a through-hole 153A in a central portion of the seal member 153. The seal member 153 is deformable in a flexible manner. The through-hole 153A is widened by being pressed by the protective tube 67, and so the through-hole 153A can receive the drive shaft 42 and the protective tube 67. Examples of materials which can be used to form the seal member 153 include natural rubber, silicone rubber, nitrile rubber, fluororubber, or the like. However, the material is not limited to these examples of materials.

Subsequently, the operation of the ultrasound catheter 130 in the second embodiment will be described.

Similarly to the first embodiment, the ultrasound catheter 130 in the second embodiment is joined to the external drive apparatus 7. In other words, the joint 50 (refer to FIG. 6) of the hub 31 of the ultrasound catheter 130 is connected to the joint connection portion 712 of the drive unit 71. In this manner, a signal can be transmitted and received between the transducer unit 41 and the external drive apparatus 7, and the drive shaft 42 can be rotated at the same time. Then, as the clamp portion 167 of the unit connector proximal portion 160 fits the holding portion 73, the joining processing is completed. In the second embodiment, the clamp portion 167 which fits the holding portion 73 is provided in the unit connector proximal portion 160 (the second connector) instead of the unit connector distal portion 142. When the clamp portion 167 is provided in the unit connector distal portion 142, the unit connector proximal portion 160 is disposed between the holding portion 73 of the external drive apparatus 7 and the joint connection portion 712. Therefore, in order to maintain a relatively long movable distance for the inner tube 34 with respect to the outer tube 140, it may be necessary to shorten the length of the anti-kink protector 57 which is attached to the hub main body 55. However, as the clamp portion 167 is provided in the unit connector proximal portion 160, it is unlikely to be necessary to shorten the length of the anti-kink protector 57, and thus, it is possible to effectively exhibit the effect of the anti-kink protector 57.

In addition, in the second embodiment, in a manner different from the first embodiment, the male screw portion 145 of the unit connector distal portion 142 is positioned to be arranged in the axial direction with respect to the male connector 146 instead of outward in the radial direction, and the female screw portion 161 of the unit connector proximal portion 160 is positioned to be arranged in the axial direction with respect to the female connector 162 instead of outward in the radial direction, and so it is possible to decrease the outer diameter of the unit connector. Therefore, when a force acts on the outer circumferential surface of the unit connector distal portion 142 or the unit connector proximal portion 160, and a force acts in a direction in which the unit connector distal portion 142 and the unit connector proximal portion 160 are loosened, compared to a case of having a greater outer diameter, it is possible to minimize torque generated with respect to the same acting force and to be prevented from being erroneously detached.

Subsequently, the drive unit 71 is moved in the distal direction or toward the distal side along the groove rail 76 on the base 75, and the inner tube 34 is thrust into (inserted into) the outer tube 140 all the way to the end. Then, the sheath 2 is inserted into a human body, and the insertion stops when the distal end of the sheath 2 passes over a target lesion.

Subsequently, in a state where the position of the sheath 2 is fixed, the pull-back operation is performed while the drive shaft 42 is rotated by the drive unit 71 so that images of the lumen in the axial direction are acquired.

Then, when performing the pull-back operation, as illustrated in FIG. 18, since the inner diameter of the first inner diameter portion 143B of the unit connector distal portion 142 is smaller than the inner diameter of the outer tube main body 141, the stopper 341 which is formed in the inner tube 34 can move into the first inner diameter portion 143B from the outer tube main body 141 without being caught. Accordingly, movement of the ultrasound transducer 411 is smooth, and no disturbance such as jumping and the like occurs in an image. Thus, it is possible to acquire favorable images. Moreover, since the inner diameter of the guidance portion 166 of the unit connector proximal portion 160 is widened in a tapered manner toward the distal side or distal direction, the stopper 341 on the inner tube 34 can move to the second inner diameter portion 163 through the guidance portion 166 without being caught. Accordingly, movement of the ultrasound transducer 411 is smooth, and no disturbance such as jumping and the like occurs in an image. Thus, it is possible to acquire favorable images.

Then, after the pull-back operation, the hub 31 is thrust or moved in the distal side (distal direction) again, and the imaging core 4 is caused to move forward. In this case, since the outer diameter of the outer circumferential surface of the stopper 341 in the inner tube decreases in a distal end direction, the stopper 341 can smoothly move without being caught inside the unit connector.

Thereafter, the ultrasound catheter 130 is operated to be pulled out of the inside of the lumen in the living body. However, when it becomes difficult to move the ultrasound catheter 130 along the guide wire 25 due to an occurrence of the so-called "trapping" or the like, an operator rotates the unit connector proximal portion 160 of the ultrasound catheter 130 with respect to the unit connector distal portion 142, and thus, it is possible to separate the male screw portion 145 from the female screw portion 161 and to disconnect the male connector 146 from the female connector 162. In this case, since the male screw portion 145 is the trapezoid-threaded screw, and the screw thread has a relatively long pitch, the male screw portion 145 can be separated from the female screw portion 161 by a relatively small number of rotations. Therefore, for example, it is possible to perform prompt measures in case of emergency such as an occurrence of "trapping" described above, for example, thereby enhancing working properties.

Figure 19:
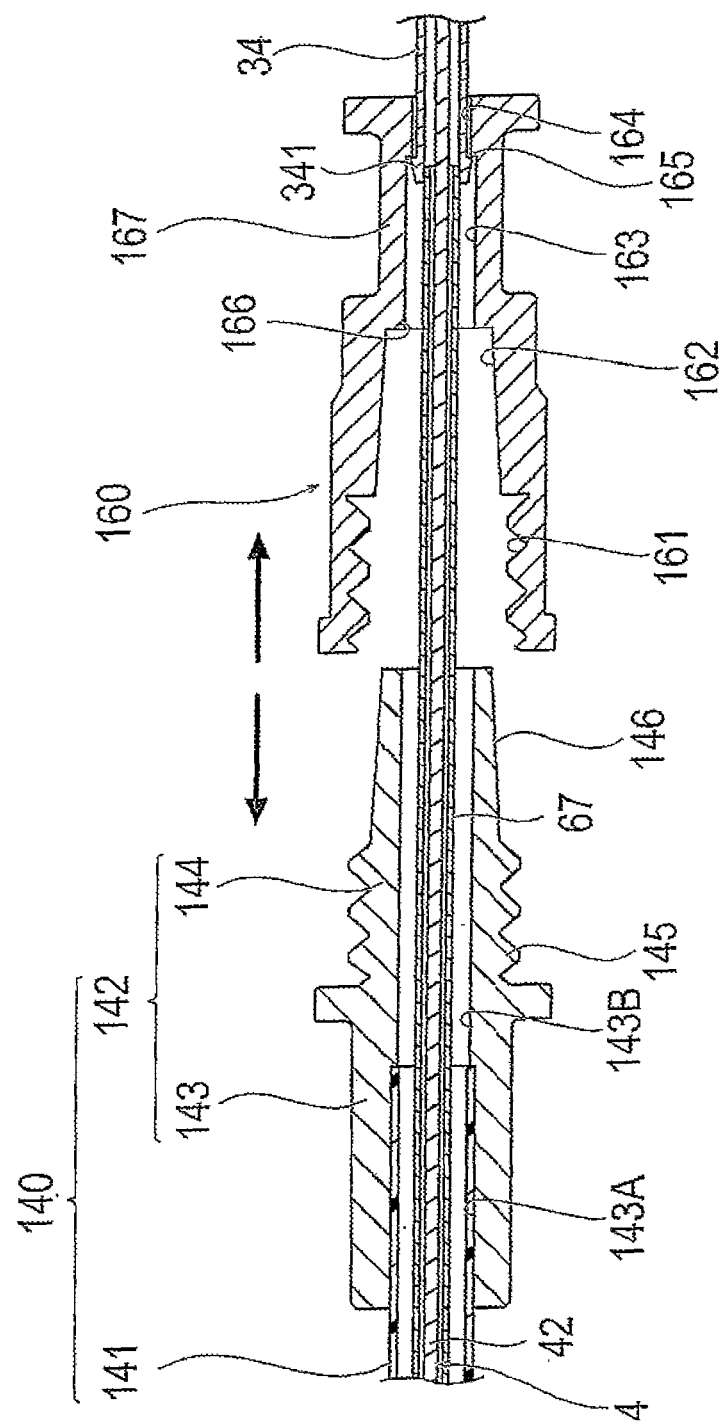
FIG. 19 is a cross-sectional view in the longitudinal direction illustrating a state where a unit connector proximal portion is disconnected from a unit connector distal portion of the ultrasound catheter in the second embodiment.

Then, when the hub 31 together with the entirety of the external drive apparatus 7 is moved to the proximal side (pulled in the proximal or rearward direction) while the outer tube 140 is grasped and fixed, the inner tube 34, the protective tube 67, the imaging core 4, and the unit connector proximal portion 160 move to the proximal side (in the proximal direction) together with the hub 31 as illustrated in FIG. 19. When the hub 31 is moved to the proximal side further, the protective tube 67 and the imaging core 4 are pulled out of the sheath 2 and the outer tube 140.

Thereafter, the wire W which is a separately prepared guide wire or the like is inserted into the lumen in which the imaging core 4 was disposed, through the opening portion in the unit connector distal portion 142 on the proximal side. In this case, since the tapered slope portion 156A is formed on the inner circumferential surface of the spacer 152, the wire W inserted through the outer tube 140 can be smoothly inserted into the sheath tube 22.

After the wire W is caused to arrive at the distal portion of the sheath 2, force is applied to the inside of the sheath 2 by using the wire W, and the sheath 2 and the guide wire 25 are operated. Thus, the sheath 2 and the guide wire 25 can return to an appropriate state. Accordingly, the sheath 2 and the guide wire 25 can be pulled out of the lumen.

Figure 20:
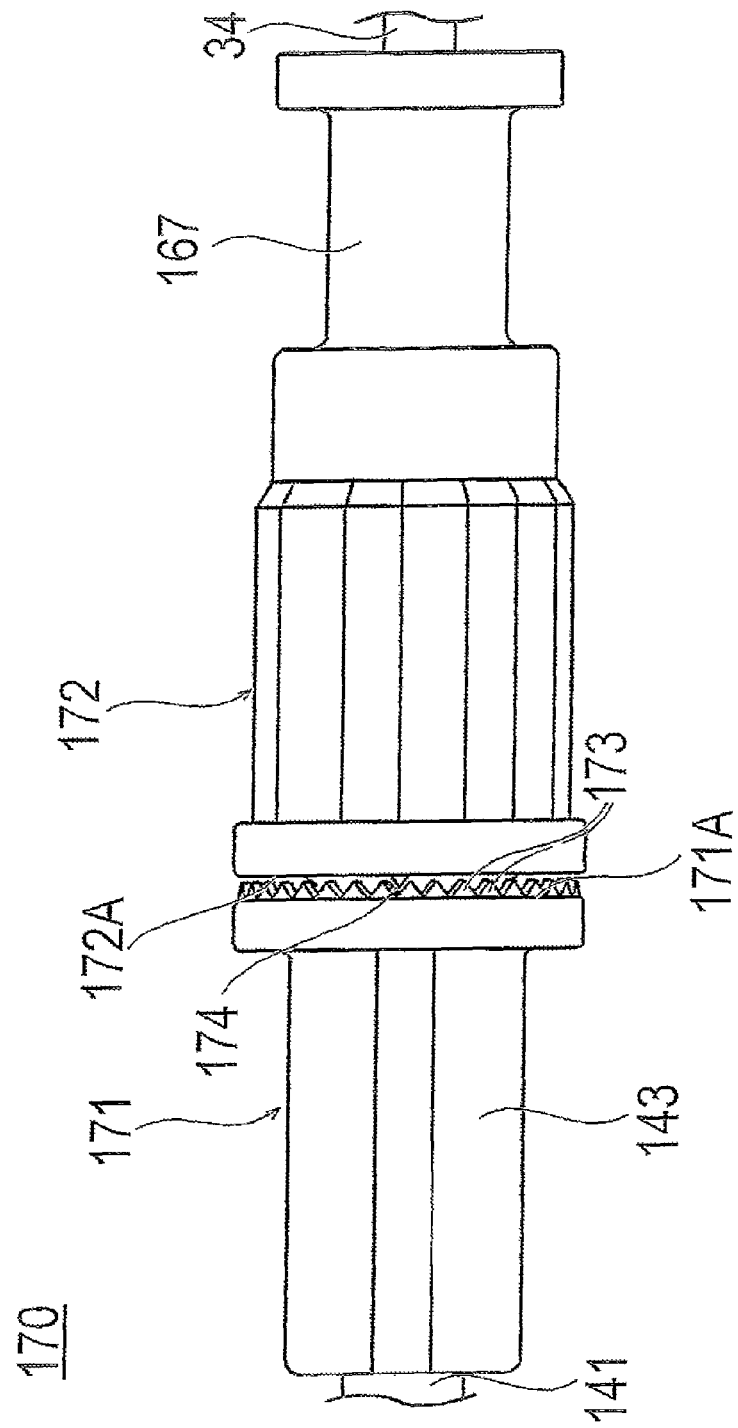
FIG. 20 is a plan view illustrating a unit connector distal portion and a unit connector proximal portion of an ultrasound catheter in a third embodiment.
Figure 21:
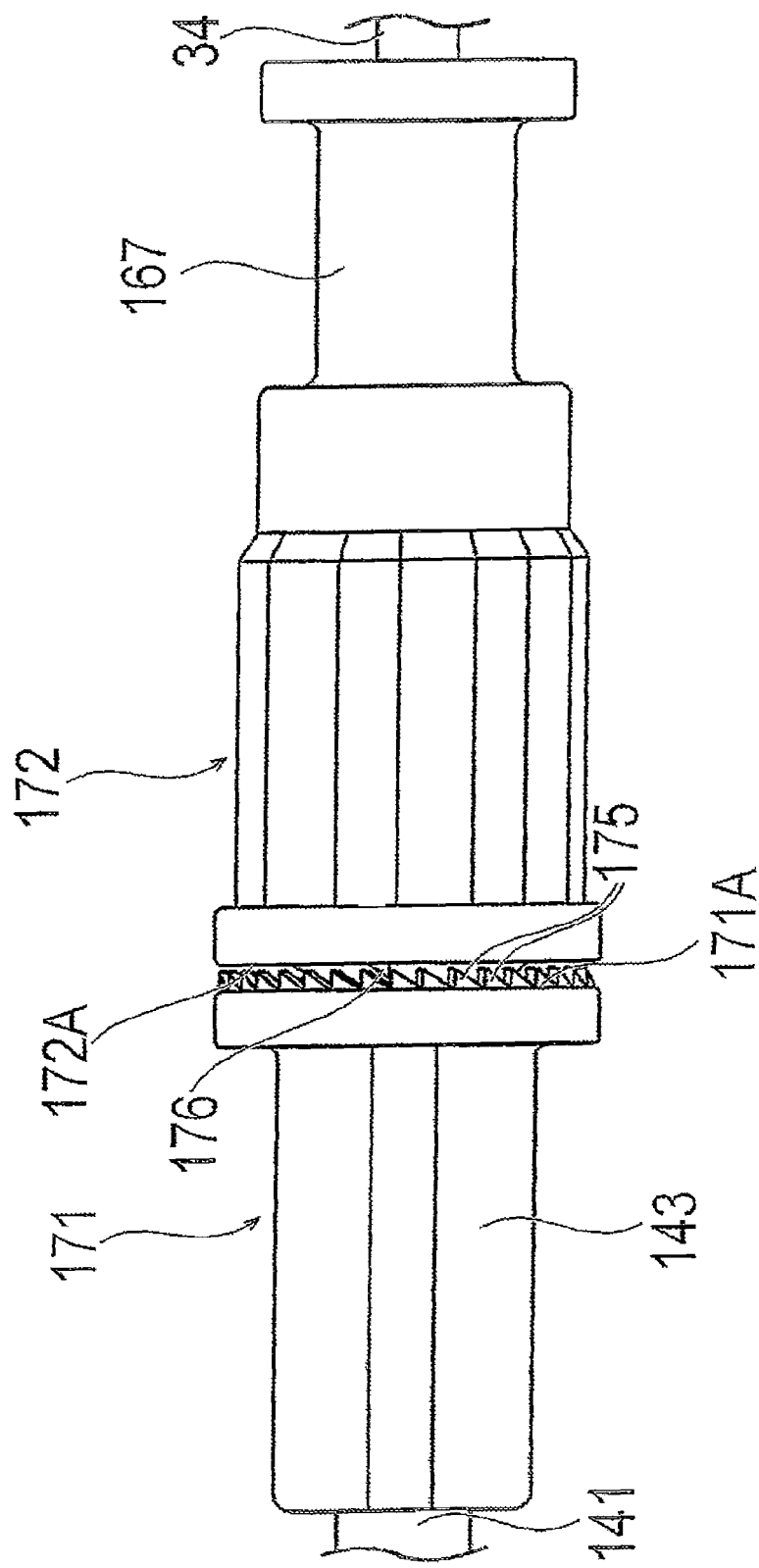
FIG. 21 is a plan view illustrating a modification example of the ultrasound catheter in the third embodiment.

FIGS. 20 and 21 illustrate an ultrasound catheter according to a third embodiment, representing another example of the inventive catheter disclosed here. The ultrasound catheter 170 according to the third embodiment is different from the second embodiment only in that a structure for preventing a unit connector distal portion 171 and a unit connector proximal portion 172 from being loosened is provided. Features in this third embodiment that are the same as in the embodiments described above are identified by common reference numerals and a detailed description of such features is not repeated.

In the ultrasound catheter 170 according to the third embodiment, as illustrated in FIG. 20, a plurality of axially-projecting teeth 173 are provided on a proximal end surface 171A of the outer tube fixing portion 143 of a unit connector distal portion 171 in a circumferential direction, and at least one axially-directed convex portion 174 configured to mesh individually with the teeth 173 of the proximal end surface 171A is formed on a distal end surface 172A of the unit connector proximal portion 172, that is, the distal end surface 172A facing the proximal end surface 171A of the outer tube fixing portion 143. The axially-facing convex portion 174 of the distal end surface 172A of the unit connector proximal portion 172 meshes with any one of the axially-projecting teeth 173 of the proximal end surface 171A of the outer tube fixing portion 143 so as to be caught thereby in a state where the unit connector proximal portion 172 is connected to the unit connector distal portion 171. Therefore, in order to loosen connection between the unit connector distal portion 171 and the unit connector proximal portion 172, there is a need to have rotary force sufficient for the convex portion 174 to ride over the teeth 173. Therefore, for example, in a case of being erroneously in contact with the unit connector during a manipulation, connection between the unit connector distal portion 171 and the unit connector proximal portion 172 can be prevented from being loosened due to unexpected force, thereby improving reliability and safety.

The force for preventing the unit connector distal portion 171 and the unit connector proximal portion 172 from being loosened can be suitably set based on slope angles with respect to the distal end surface 172A and the proximal end surface 171A of the teeth 173 and the convex portion 174. For example, as described in the modification example illustrated in FIG. 21, in a case of significant slope angles of portions with which teeth 175 and a convex portion 176 come into contact when the unit connector distal portion 171 and the unit connector proximal portion 172 are rotated in a direction to be loosened, significant force is necessary in order to loosen the connection. However, it is possible to improve the reliability and the safety.

In addition, in the third embodiment, the plurality of teeth 173 are formed in the unit connector distal portion 171 and at least one convex portion 174 is formed in the unit connector proximal portion 172. However, a convex portion may be formed in the unit connector distal portion, and teeth may be formed in the unit connector proximal portion.

The above-described ultrasound catheter 170 according to the third embodiment is provided with the male connector 146 and the female connector 162 for generating a fitting force (friction force) by utilizing a wedge effect. However, since there is provided the structure (the teeth 173 and the convex portion 174) for preventing the unit connector distal portion 171 and the unit connector proximal portion 172 from being loosened, unless it is intended to maintain a higher fitting force in a fitting portion, the male connector 146 and the female connector 162 do not need to also be provided.

An ultrasound catheter 180 according to a fourth embodiment is different from the second embodiment in only the point that a structure for preventing a unit connector distal portion 181 and a unit connector proximal portion 182 from being loosened is provided. The same reference numerals and signs are applied to the portions having the same function as those in the first and second embodiments, and descriptions thereof will be omitted.

Figure 22:
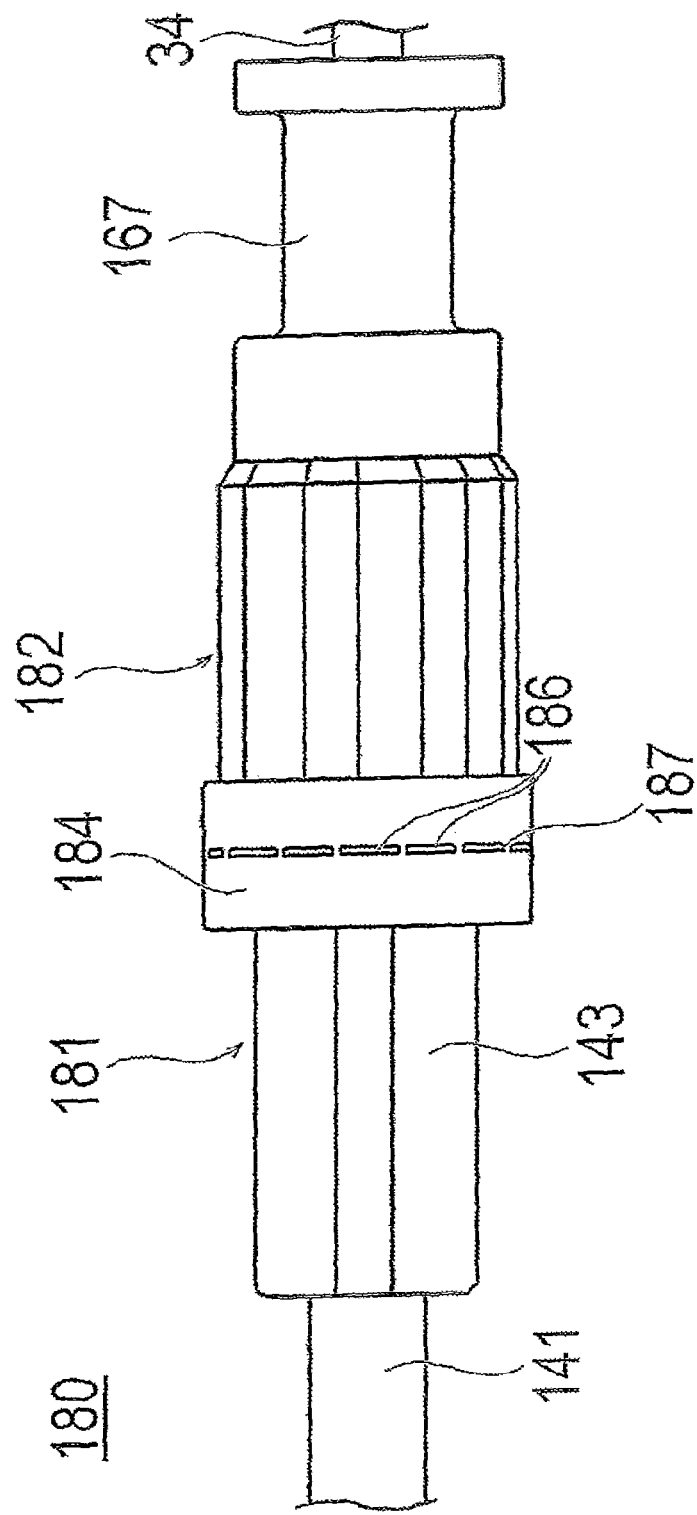
FIG. 22 is a plan view illustrating a state before a unit connector distal portion and a unit connector proximal portion of an ultrasound catheter in a fourth embodiment are connected to each other.
Figure 23:
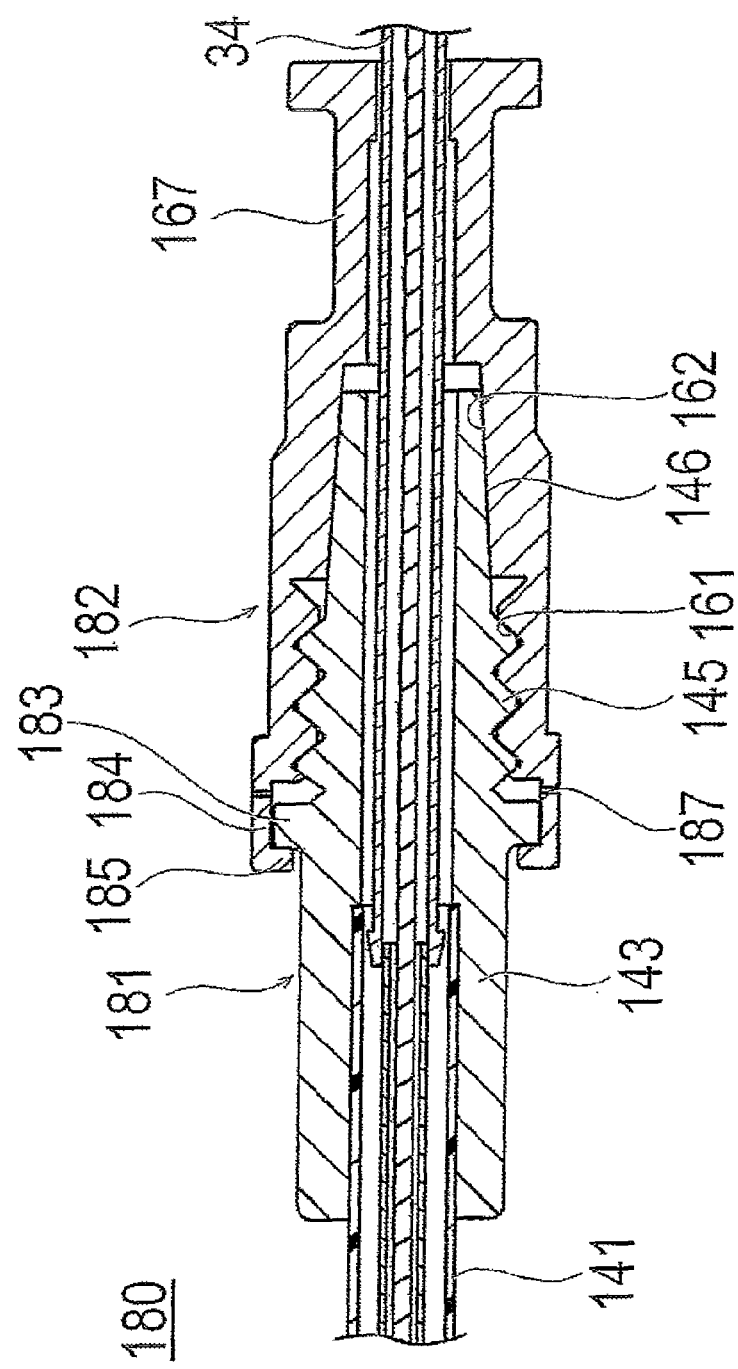
FIG. 23 is a cross-sectional view in the longitudinal direction illustrating a state where the unit connector distal portion and the unit connector proximal portion of the ultrasound catheter in the fourth embodiment are connected to each other.
Figure 24:
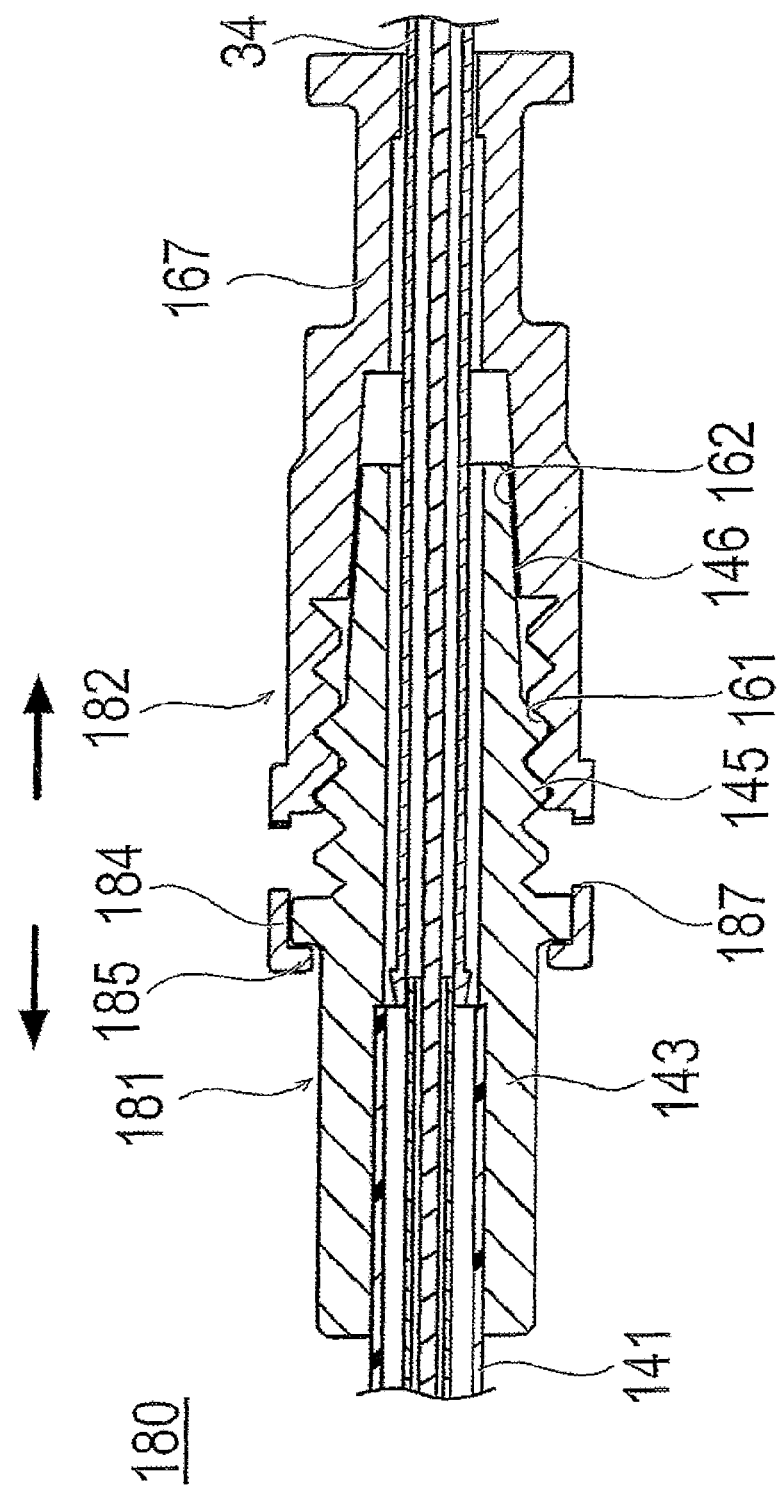
FIG. 24 is a cross-sectional view in the longitudinal direction illustrating a state where the unit connector distal portion and the unit connector proximal portion of the ultrasound catheter in the fourth embodiment are disconnected from each other.

FIGS. 22-24 illustrate an ultrasound catheter according to a fourth embodiment, representing another example of the inventive catheter disclosed here. In the ultrasound catheter 180 according to the fourth embodiment, as illustrated in FIGS. 22 and 23, an annular convex portion 183 extending in the circumferential direction is formed on the outer circumferential surface of the outer tube fixing portion 143 of the unit connector distal portion 181, and an annular joining portion 184 extending in the distal end direction and covering the outside surface of (axially overlapping) the annular convex portion 183 is formed in the unit connector proximal portion 182 on the distal side. A radially inwardly projecting engagement portion 185 protruding toward the central axis so as to be caught by the annular convex portion 183 is provided at the distal end of the annular joining portion 184 and is positioned on the distal side of the annular convex portion 183. The engagement portion 185 engages the annular convex portion 183 in a state where the male screw portion 145 is screwed into the female screw portion 161 and the unit connector proximal portion 182 is connected to the unit connector distal portion 181.

In addition, a plurality of perforation-like holes 186 are arranged in the circumferential direction and are formed in the annular joining portion 184 on the proximal side from the engagement portion 185. A breakage portion 187 is formed between the circumferentially adjacent holes 186.

The engagement portion 185 engages the annular convex portion 183 in a state where the male screw portion 145 is screwed into the female screw portion 161 and the unit connector proximal portion 182 is connected to the unit connector distal portion 181. Therefore, for example, in a case of being erroneously in contact with the unit connector during a manipulation, connection between the unit connector distal portion 181 and the unit connector proximal portion 182 can be prevented from being erroneously loosened due to an unexpected force, thereby improving the reliability and the safety. Then, when the unit connector distal portion 181 and the unit connector proximal portion 182 are relatively rotated, the breakage portions 187 are broken and the engagement portion 185 is disconnected from the unit connector proximal portion 182 as illustrated in FIG. 24, and thus, the unit connector distal portion 181 and the unit connector proximal portion 182 can be disconnected from each other.

The above-described ultrasound catheter 180 according to the fourth embodiment is provided with the male connector 146 and the female connector 162 for generating fitting force (friction force) by utilizing a wedge effect. However, since there is provided the structure (the engagement portion 185 and the annular convex portion 183) for preventing the unit connector distal portion 181 and the unit connector proximal portion 182 from being loosened, unless it is intended to maintain a higher fitting force in the fitting portion, the male connector 146 and the female connector 162 do not need to be also provided.

Figure 25:
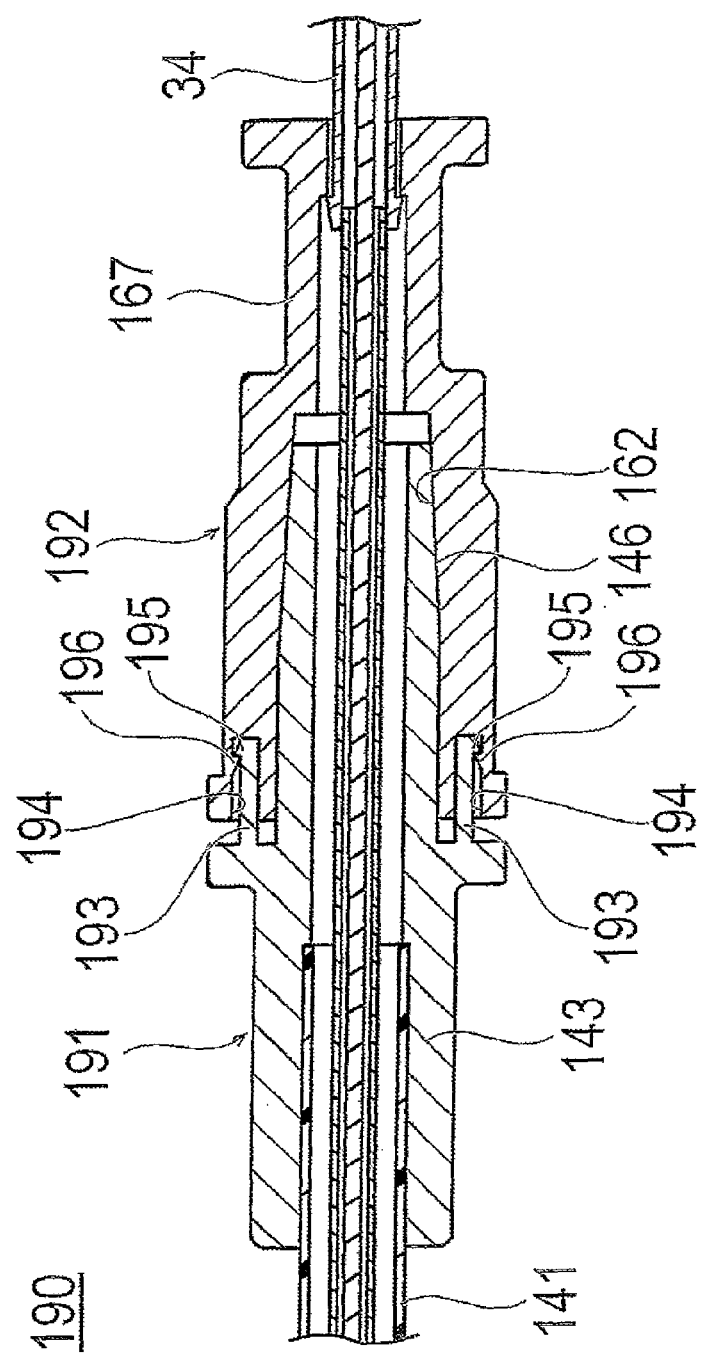
FIG. 25 is a cross-sectional view in the longitudinal direction illustrating a state where a unit connector distal portion and a unit connector proximal portion of an ultrasound catheter in a fifth embodiment are connected to each other.
Figure 26:
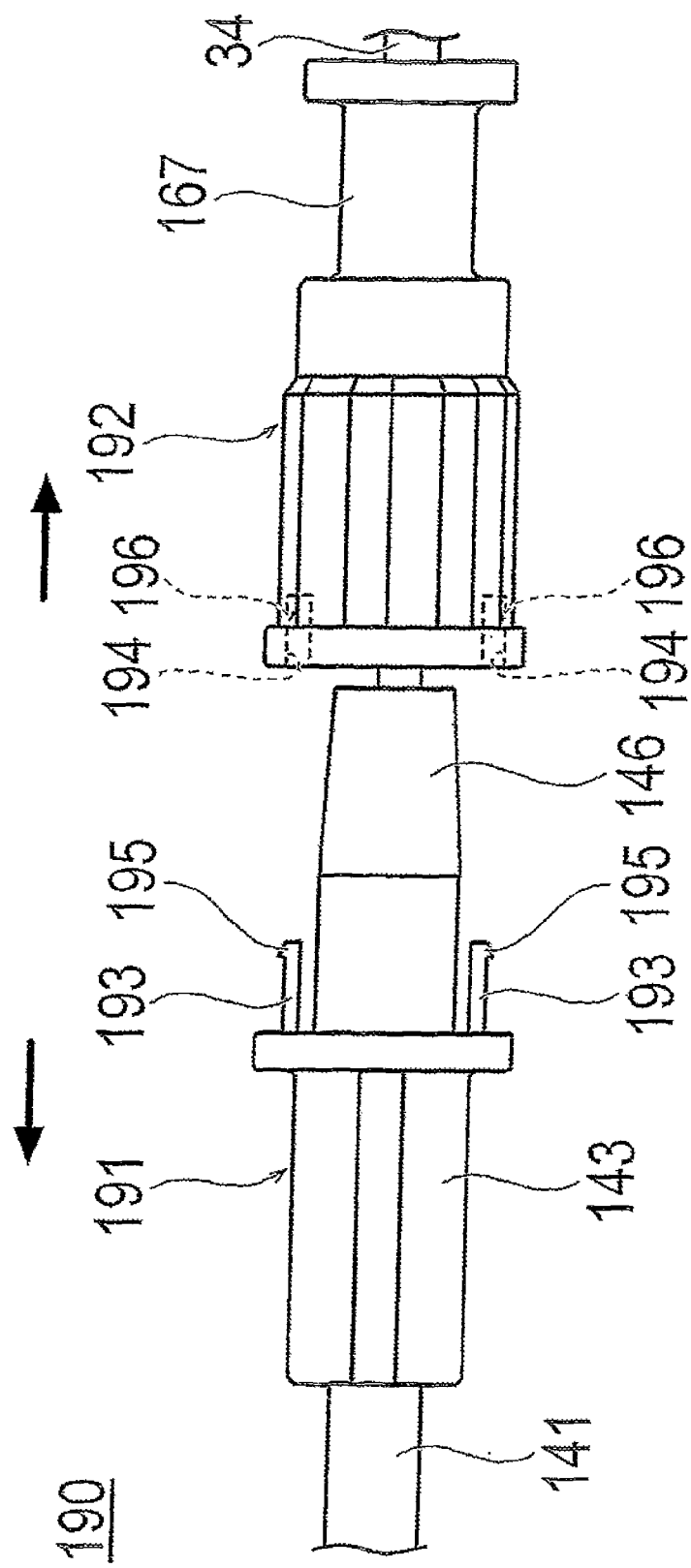
FIG. 26 is a cross-sectional view in the longitudinal direction illustrating a state where the unit connector distal portion and the unit connector proximal portion of the ultrasound catheter in the fifth embodiment are disconnected from each other.

FIGS. 25 and 26 illustrate an ultrasound catheter according to a fifth embodiment, representing another example of the inventive catheter disclosed here. The ultrasound catheter 190 according to the fifth embodiment is different from the second embodiment only in that a structure for preventing a unit connector distal portion 191 and a unit connector proximal portion 192 from being loosened is provided, and no female screw portion or male screw portion to be screwed to each other is provided. Features in this fifth embodiment that are the same as in the first and second embodiments are identified by common reference numerals and a detailed description of such features is not repeated here.

In the ultrasound catheter 190 according to the fifth embodiment, as illustrated in FIG. 25, at least one convex portion 193 (two in the present embodiment) extending axially in the proximal end direction from the outer tube fixing portion 143 of the unit connector distal portion 191 is formed, and an axially recessed concave portion 194 into which the convex portion 193 is fitted is formed on the distal side of the unit connector proximal portion 192. A first engagement claw 195 is formed at the distal end of the convex portion 193, and a second engagement claw 196 by which the first engagement claw 195 is caught is formed inside the concave portion 194. In a state where the unit connector proximal portion 192 is connected to the unit connector distal portion 191, the convex portion 193 fits into or is received in the concave portion 194, and the first engagement claw 195 and the second engagement claw 196 engage each other.

In a state where the unit connector proximal portion 192 is connected to the unit connector distal portion 191, the first engagement claw 195 engages the second engagement claw 196. Therefore, for example, in a case of being erroneously in contact with the unit connector during a manipulation, connection between the unit connector distal portion 191 and the unit connector proximal portion 192 can be prevented from being erroneously loosened due to unexpected force, thereby improving the reliability and the safety. In addition, as the convex portion 193 fits the concave portion 194, the unit connector distal portion 191 and the unit connector proximal portion 192 can be coaxially connected to each other.

Then, when the unit connector distal portion 191 and the unit connector proximal portion 192 are moved in a direction of being separated from each other, the first engagement claw 195 and the second engagement claw 196 are disengaged from each other due to deformation or destruction as illustrated in FIG. 26, and thus, the unit connector distal portion 191 and the unit connector proximal portion 192 can be disconnected from each other.

The above-described ultrasound catheter 190 according to the fifth embodiment is provided with the male connector 146 and the female connector 162 for generating fitting force (friction force) by utilizing a wedge effect. However, since there is provided the structure (the first engagement claw 195 and the second engagement claw 196) for preventing the unit connector distal portion 191 and the unit connector proximal portion 192 from being loosened, unless it is intended to maintain higher fitting force in the fitting portion, the male connector 146 and the female connector 162 do not also need to be provided.

Figure 27:
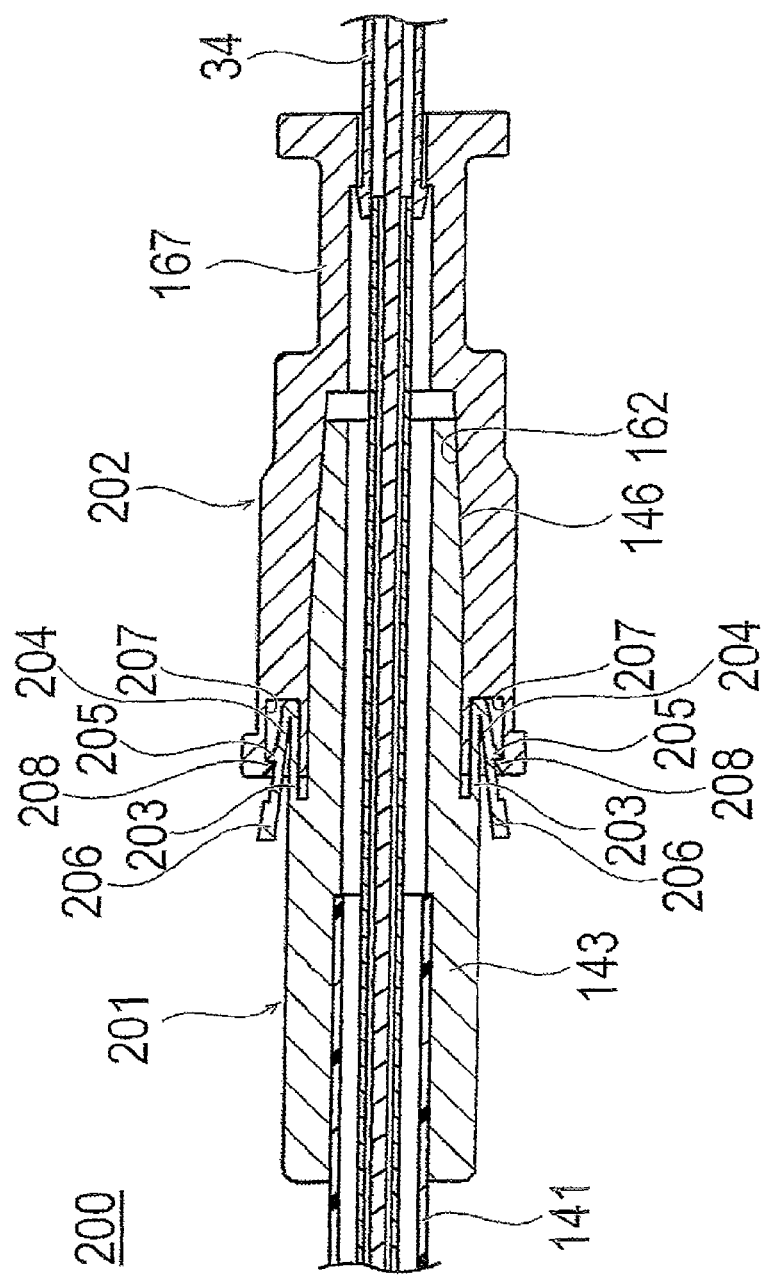
FIG. 27 is a cross-sectional view in the longitudinal direction illustrating a state where a unit connector distal portion and a unit connector proximal portion of an ultrasound catheter in a sixth embodiment are connected to each other.
Figure 28:
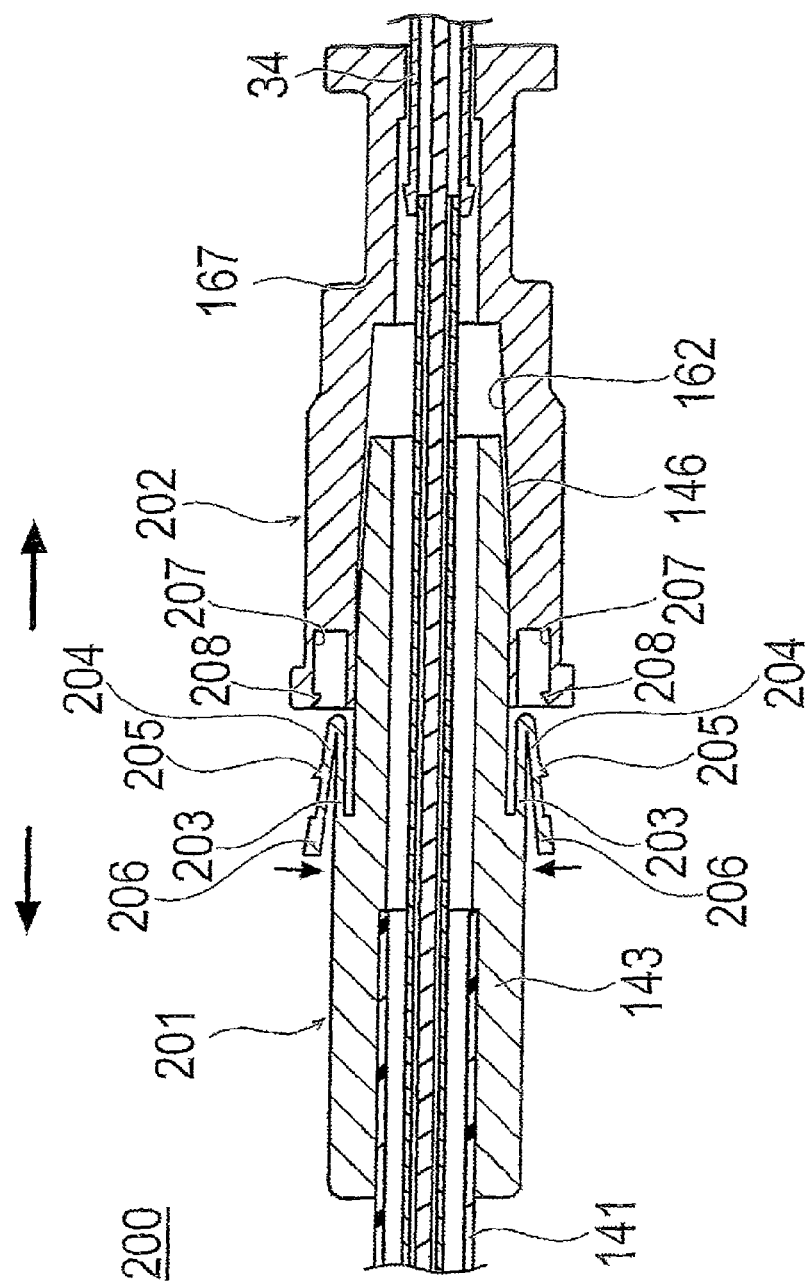
FIG. 28 is a cross-sectional view in the longitudinal direction illustrating a state where the unit connector distal portion and the unit connector proximal portion of the ultrasound catheter in the sixth embodiment are disconnected from each other.

FIGS. 27 and 28 illustrate an ultrasound catheter according to a sixth embodiment, representing another example of the inventive catheter disclosed here. An ultrasound catheter 200 according to the sixth embodiment is different from the second embodiment only in that a structure for preventing a unit connector distal portion 201 and a unit connector proximal portion 202 from being loosened is provided, and no female screw portion or male screw portion to be screwed to each other is provided. Features in this sixth embodiment that are the same as in the first and second embodiments are identified by common reference numerals and a detailed description of such features is not repeated here.

In the ultrasound catheter 200 according to the sixth embodiment, as illustrated in FIG. 27, at least one convex portion 203 (two in the present embodiment) extends in the proximal end direction from the outer tube fixing portion 143 of the unit connector distal portion 201, and a turned-back portion 204 is turned back from the protruding distal end of the convex portion 203. The turned-back portion 204 includes a first engagement claw 205 protruding outward in the radial direction and a press portion 206 for moving the first engagement claw 205 backward by being pressed by an operator so as to warp the turned-back portion 204.

A concave portion 207 into which the convex portion 203 is fitted is formed in the unit connector proximal portion 202 on the distal side, and a second engagement claw 208 by which the first engagement claw 205 is caught is formed inside the concave portion 207. In a state where the unit connector proximal portion 202 is connected to the unit connector distal portion 201, the convex portion 203 is fitted in the concave portion 207, and the first engagement claw 205 and the second engagement claw 208 engage each other.

In a state where the unit connector proximal portion 202 is connected to the unit connector distal portion 201, the first engagement claw 205 engages the second engagement claw 208. Therefore, for example, in a case of being erroneously in contact with the unit connector during a manipulation, connection between the unit connector distal portion 201 and the unit connector proximal portion 202 are prevented from being erroneously loosened due to unexpected force, thereby improving the reliability and the safety. In addition, as the convex portion 203 fits the concave portion 207, the unit connector distal portion 201 and the unit connector proximal portion 202 are coaxially connected to each other.

Then, as illustrated in FIG. 28, when the press portion 206 is pressed, the turned-back portion 204 is warped and the first engagement claw 205 is separated from the second engagement claw 208, thereby being disengaged from each other. In this state, when the unit connector distal portion 201 and the unit connector proximal portion 202 are moved in a direction of being separated from each other, the unit connector distal portion 201 and the unit connector proximal portion 202 are disconnected from each other.

The above-described ultrasound catheter 200 according to the sixth embodiment is provided with the male connector 146 and the female connector 162 for generating a fitting force (friction force) by utilizing a wedge effect. However, since there is provided the structure (the first engagement claw 205 and the second engagement claw 208) for preventing the unit connector distal portion 201 and the unit connector proximal portion 202 from being loosened, unless it is intended to maintain a higher fitting force in the fitting portion, the male connector 146 and the female connector 162 do not need to also be provided.

Figure 29:
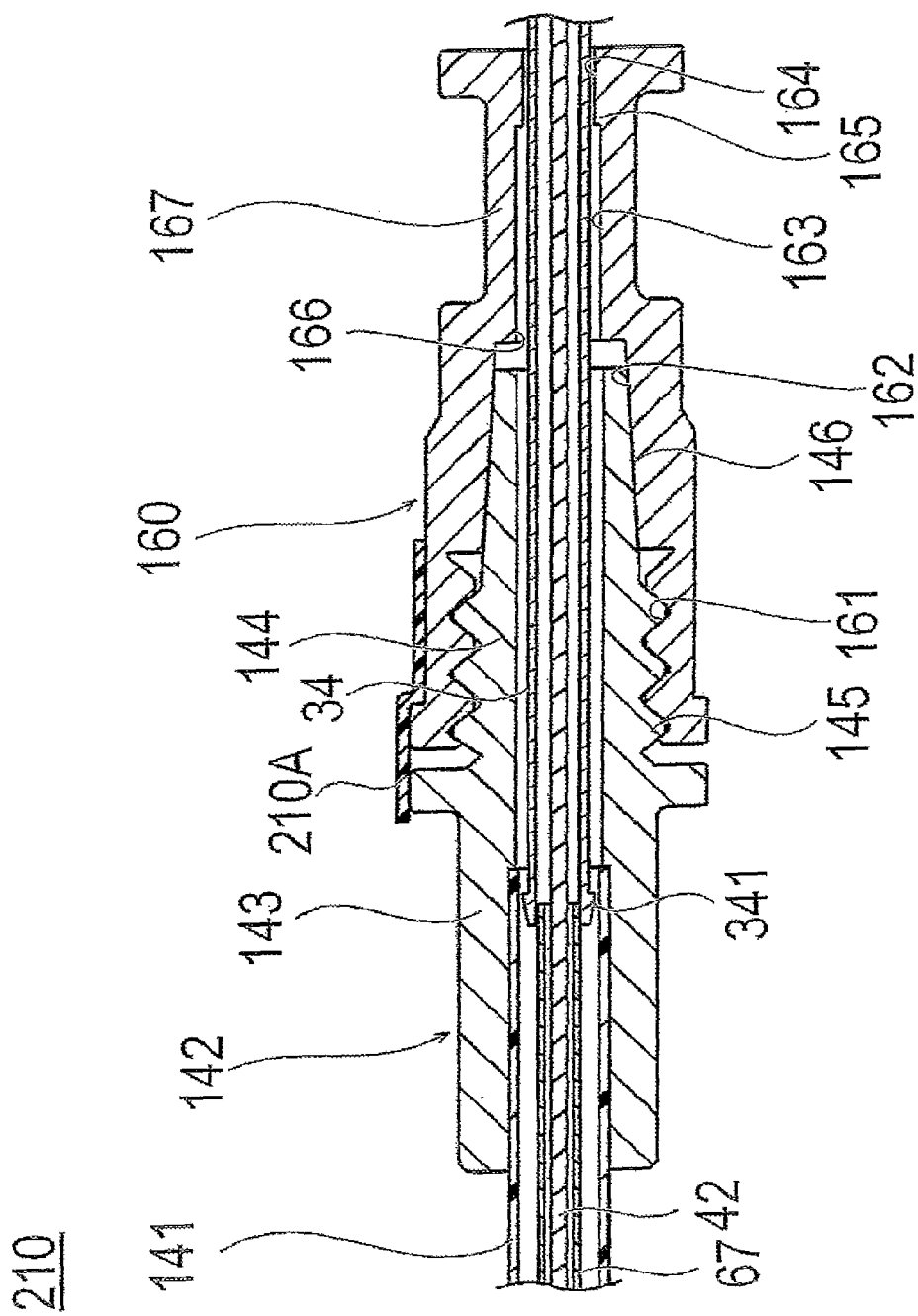
FIG. 29 is a cross-sectional view in the longitudinal direction illustrating a state where a unit connector distal portion and a unit connector proximal portion of an ultrasound catheter in a seventh embodiment are connected to each other.
Figure 30:
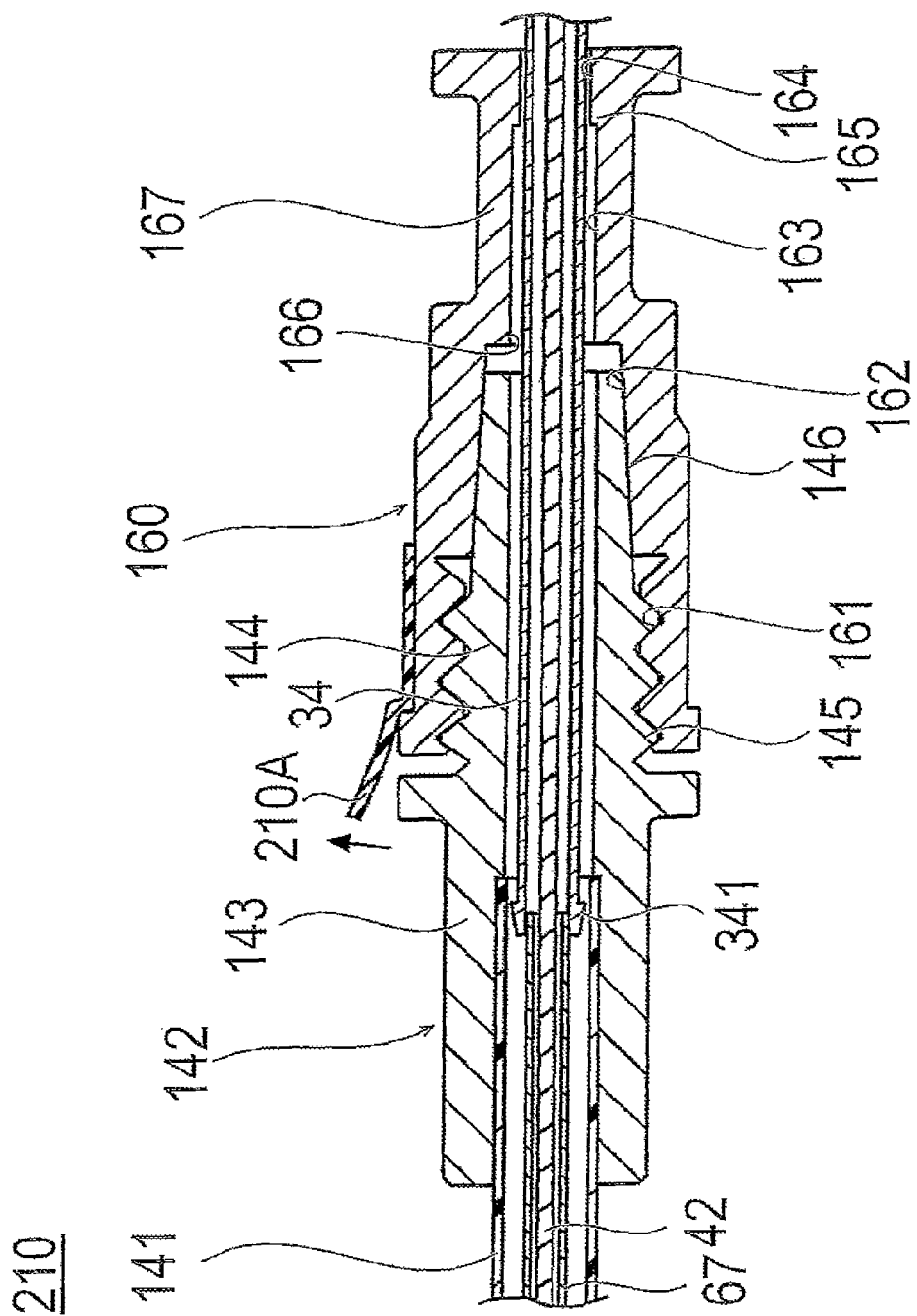
FIG. 30 is a cross-sectional view in the longitudinal direction illustrating a state where the unit connector distal portion and the unit connector proximal portion of the ultrasound catheter in the seventh embodiment are disconnected from each other.

FIGS. 29 and 30 illustrate an ultrasound catheter according to a seventh embodiment, representing another example of the inventive catheter disclosed here. The ultrasound catheter 210 according to the seventh embodiment is different from the second embodiment only in that a structure for preventing the unit connector distal portion 142 and the unit connector proximal portion 160 from being loosened is added. Features in this seventh embodiment that are the same as in the first and second embodiments are identified by common reference numerals and a detailed description of such features is not repeated here.

In the ultrasound catheter 210 according to the seventh embodiment, as illustrated in FIG. 29, the outer tube fixing portion 143 of the unit connector distal portion 142 and the unit connector proximal portion 160 are joined to each other by a tape 210A which is provided with a glue or an adhesive on one surface in a peelable manner (bonded in a way that permits subsequent separation). The material of the tape 210A is not particularly limited as long as the material can be peelably pasted.

Then, as illustrated in FIG. 30, when the tape 210A is caused to peel off, and the unit connector distal portion 142 and the unit connector proximal portion 160 are relatively rotated, the unit connector distal portion 142 and the unit connector proximal portion 160 can be disconnected from each other. In this manner, there is a need to perform an operation for peeling off the tape 210A before relatively rotating the unit connector distal portion 142 and the unit connector proximal portion 160. Therefore, for example, in a case of being erroneously in contact with the unit connector during a manipulation, connection between the unit connector distal portion 142 and the unit connector proximal portion 160 can be prevented from being erroneously loosened due to unexpected force, thereby improving the reliability and the safety.

The above-described ultrasound catheter 210 according to the seventh embodiment is provided with the male connector 146 and the female connector 162 for generating fitting force (friction force) by utilizing a wedge effect. However, since there is provided the structure (the tape 210A) for preventing the unit connector distal portion 142 and the unit connector proximal portion 160 from being loosened, unless it is intended to maintain a higher fitting force in the fitting portion, the male connector 146 and the female connector 162 do not need to be also provided.

Figure 31:
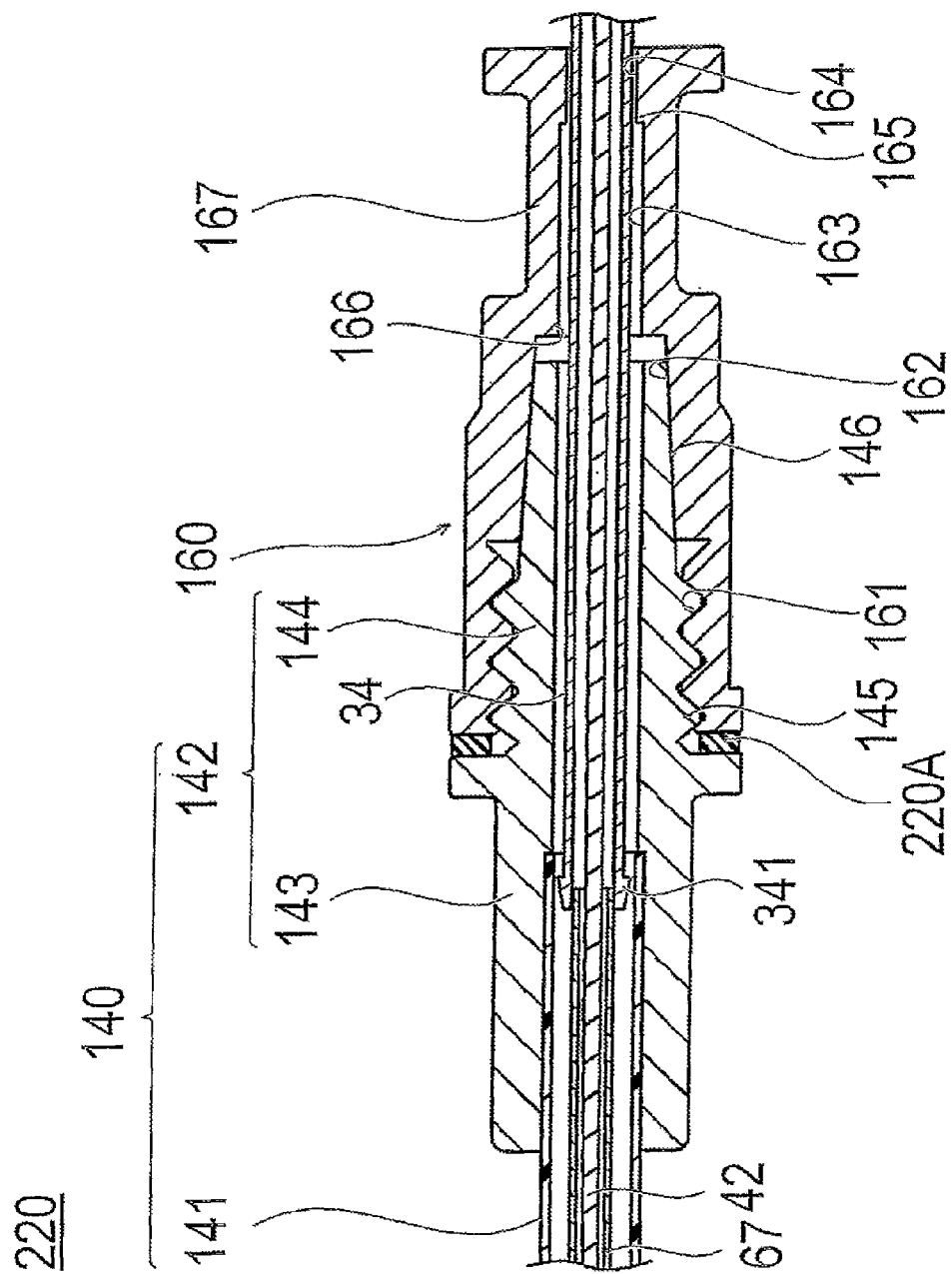
FIG. 31 is a cross-sectional view in the longitudinal direction illustrating a state where a unit connector distal portion and a unit connector proximal portion of an ultrasound catheter in an eighth embodiment are connected to each other.
Figure 32:
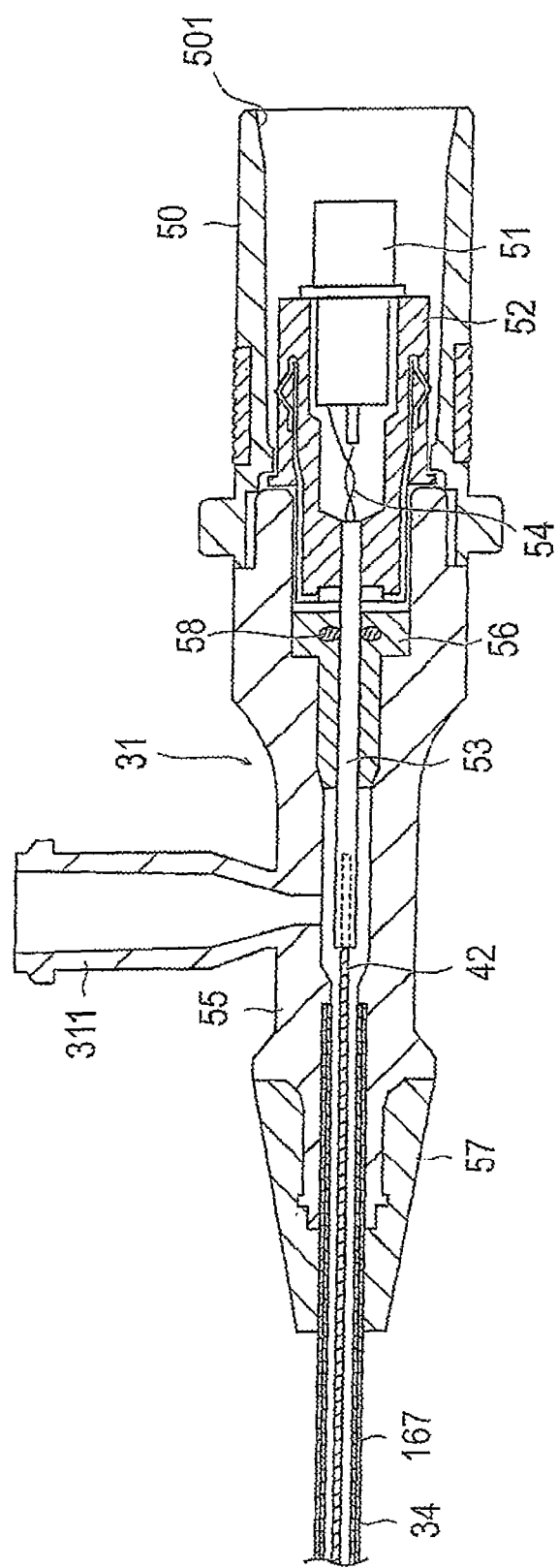
FIG. 32 is a cross-sectional view in the longitudinal direction illustrating a proximal portion of a protective tube in a modification example of the ultrasound catheter in the first embodiment.

FIGS. 31 and 32 illustrate an ultrasound catheter according to an eighth embodiment, representing another example of the inventive catheter disclosed here. The ultrasound catheter 220 according to this eighth embodiment is different from the second embodiment in only the point that the structure for preventing the unit connector distal portion 142 and the unit connector proximal portion 160 from being loosened is added. Features in this eighth embodiment that are the same as in the first and second embodiments are identified by common reference numerals and a detailed description of such features is not repeated here.

In the ultrasound catheter 220 according to the eighth embodiment, as illustrated in FIG. 31, the outer tube fixing portion 143 of the unit connector distal portion 142 and the unit connector proximal portion 160 are joined to each other by an adhesive 220A. The material of the adhesive 220A is not particularly limited as long as the material can be peelably bonded (bonded in a way that permits subsequent separation). In this manner, the unit connector distal portion 142 and the unit connector proximal portion 160 are bonded to each other by the adhesive 220A. Therefore, for example, in a case of being erroneously in contact with the unit connector during a manipulation, connection between the unit connector distal portion 142 and the unit connector proximal portion 160 can be prevented from being erroneously loosened due to unexpected force, thereby improving the reliability and the safety.

Then, when the unit connector distal portion 142 and the unit connector proximal portion 160 are relatively rotated, the adhesive 220A is caused to separate and peel off, and thus, the unit connector distal portion 142 and the unit connector proximal portion 160 can be disconnected from each other.

The above-described ultrasound catheter 220 according to the eighth embodiment is provided with the male connector 146 and the female connector 162 for generating fitting force (friction force) by utilizing a wedge effect. However, since there is provided the structure (the adhesive 220A) for preventing the unit connector distal portion 142 and the unit connector proximal portion 160 from being loosened, unless it is intended to maintain a higher fitting force in the fitting portion, the male connector 146 and the female connector 162 do not need to be also provided.

The present invention is not limited to only the above-described embodiments, and various changes can be made, and equivalents employed, by those skilled in the art within the technical ideas of the present invention. For example, the description of the above-described embodiments talks in terms of the catheter a an ultrasound catheter. However, the present invention can also be applied to an optical probe for a diagnosis apparatus (an OCT catheter) such as an optical coherence tomography diagnosis apparatus, an optical frequency domain imaging diagnosis apparatus, and the like utilizing light; an endoscope system; and the like. Moreover, the present invention can be applied to all catheters as long as the catheter has a tubular body such as the catheter and the like for performing mechanical drive, for example, a catheter which is used in directional coronary atherectomy (DCA). Therefore, in the present embodiment, liquid fills the inside the lumen of the sheath 2 in which the imaging core 4 is accommodated. However, the present invention can be applied to a catheter which is filled with no liquid.

Figure 33:
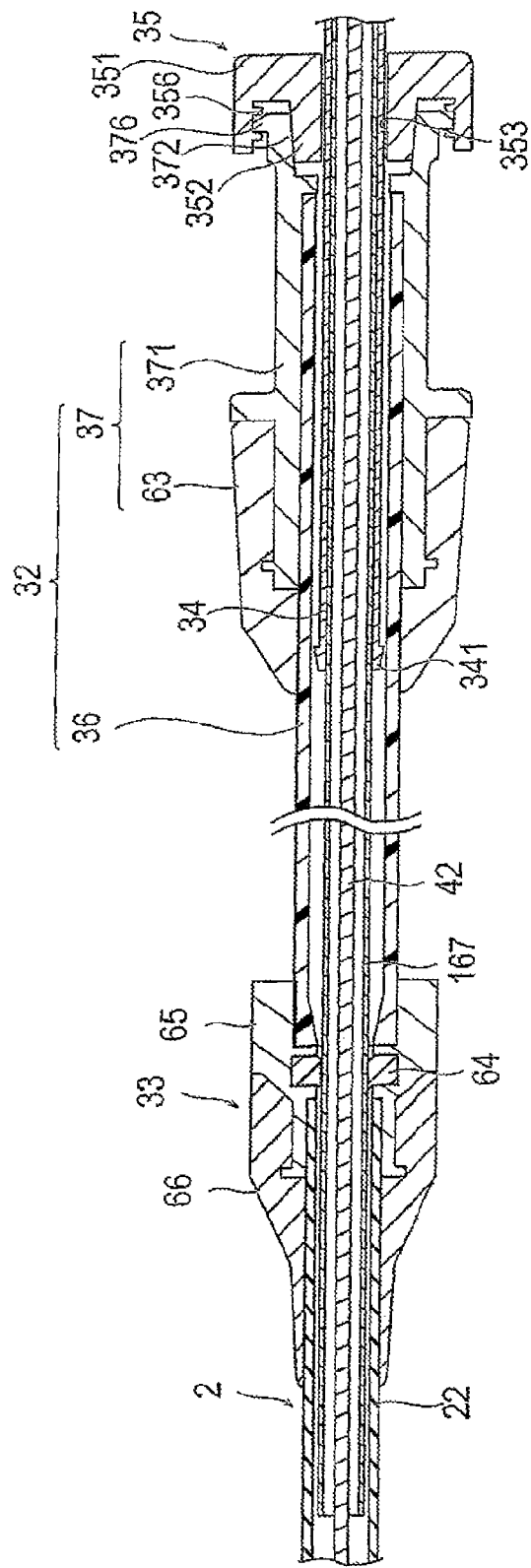
FIG. 33 is a cross-sectional view in the longitudinal direction illustrating a distal portion of the protective tube in the modification example of the ultrasound catheter in the first embodiment.

In addition, in the above-described ultrasound catheter 1 in the first embodiment, the protective tube 67 is fixed to the inner circumferential surface of the inner tube 34. However, the portion to which the protective tube is fixed is not limited to the inner circumferential surface of the inner tube 34. In addition, a protective tube 167 may be fixed to the hub 31 as described in the modification example illustrated in FIGS. 32 and 33. In addition, the protective tube may be integrally formed with the inner tube or the hub.

Figure 34:
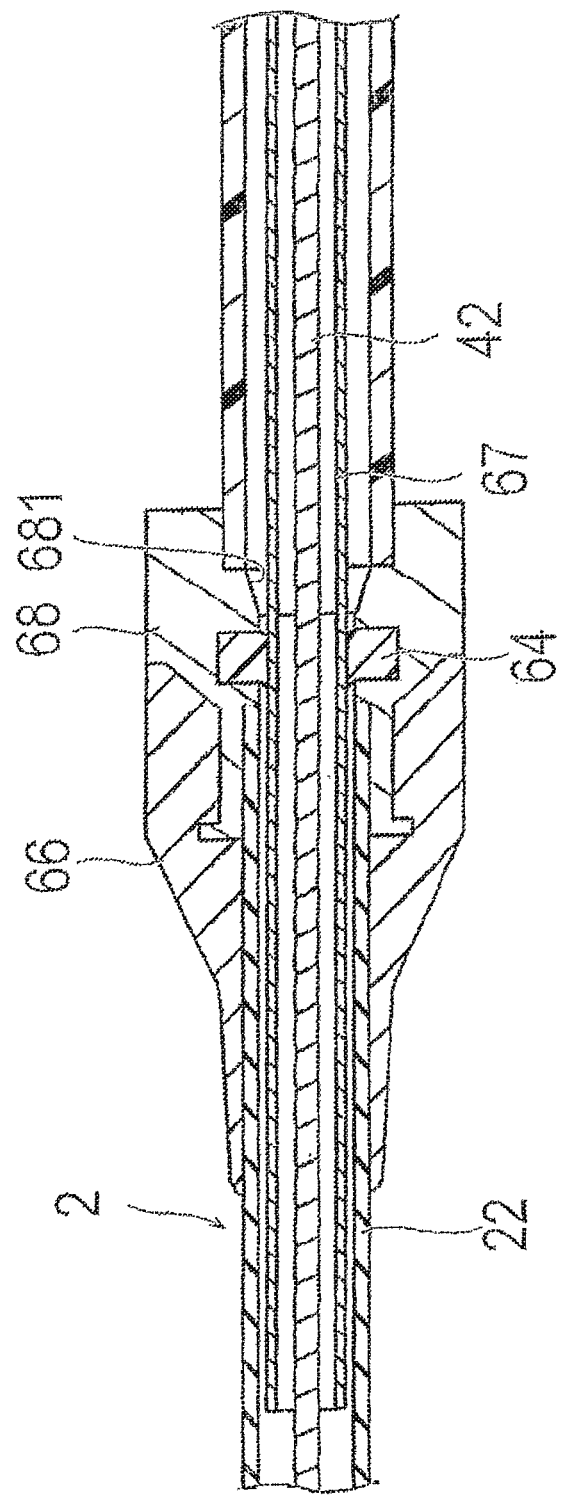
FIG. 34 is a cross-sectional view in the longitudinal direction illustrating the relay connector in an alternative modification example of the ultrasound catheter in the first embodiment.

In addition, in the above-described ultrasound catheter 1 in the first embodiment, the tapered slope portion 361 which slopes toward the axial center as being closer to the distal side is formed on the inner circumferential surface of the outer tube main body 36 on the distal side fixed to the relay connector 33. However, as disclosed in the alternative modification example illustrated in FIG. 34, a tapered slope portion 681 which slopes toward the axial center as being closer to the distal side may be formed in a relay connector 68 to which the outer tube main body is fixed.

Also, in the above-described ultrasound catheter 1 in the first embodiment, the through-hole 641 of the seal member 64 is in a sealed state by the elastic force of itself when the drive shaft 42 and the protective tube 67 are pulled out. However, for example, a mechanism for pressing the seal member may be provided so as to obtain a structure having the through-hole to be in a sealed state by compressing and deforming the seal member.

In addition, in the first embodiment, the female connector 372 is provided on the outer tube 32 side, and the male connector 352 is provided on the second connector 35 side. However, the male connector may be provided on the outer tube 32 side, and the female connector may be provided on the second connector 35 side. In addition, the structure of connection may be a screw type or an insertion type instead of the luer taper structure.

In addition, the configuration comprised in each of the above-described embodiments can be utilized by being combined, if possible.

The detailed description above describes embodiments of a catheter and operational method representing examples of the inventive catheter and operation disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A catheter comprising:
a sheath configured to be inserted into a lumen in a living body;
a drive shaft positioned in the sheath to transmit a mechanical drive force;

an axially movable hub connected to the drive shaft so that axial movement of the hub results in axial movement of the drive shaft;
an outer tube positioned proximal of the sheath and comprising a first connector at a proximal portion of the outer tube;
an axially movable inner tube positioned at least partially inside the outer tube and being connected to the hub to axially move together with the hub relative to the outer tube, the inner tube projecting distally from the hub, the inner tube possessing a distal end;
a second connector configured to be connected to and disconnected from the first connector and comprising a pass-through port configured to receive the inner tube;
a sheath connection portion connecting the sheath and the outer tube; and
a protective tube protruding distally beyond the distal end of the inner tube, the drive shaft being accommodated in the protective tube, the protective tube being positionable inside the outer tube and inside the sheath, and being removable from inside the outer tube and the sheath together with the hub and the inner tube after the second connector is disconnected from the first connector.

2. The catheter according to claim 1, further comprising an engagement portion at a distal portion of the inner tube, the engagement portion possessing an outer diameter that is enlarged relative to an outer diameter of an immediately adjoining portion of the inner tube, the pass-through port possessing an inner diameter smaller than the outer diameter of the engagement portion so that the pass-through port does not allow the engagement portion to pass through the pass-through port.

3. The catheter according to claim 2, wherein the sheath connection portion includes a seal that is in sealing contact with an outer circumferential surface of the protective tube, the protective tube being slidable relative to the seal.

4. The catheter according to claim 3, wherein the seal includes a passage through which the protective tube and the drive shaft pass, the protective tube and the drive shaft being removable from the passage when the hub is axially moved in the proximal direction, the passage being configured to automatically close when the protective tube and the drive shaft are pulled-out from the passage.

5. The catheter according to claim 1, wherein the protective tube is fixed to the inner tube so that axial movement of the inner tube results in axial movement of the protective tube.

6. The catheter according to claim 1, wherein the protective tube is fixed to the hub.

7. The catheter according to claim 1, wherein the protective tube is a tubular body which is impermeable to liquid.

8. The catheter according to claim 1, wherein an inner circumferential surface of at least one of the outer tube and the sheath connection portion slopes inwardly in a distal direction.

9. The catheter according to claim 1, wherein the sheath connection portion includes a seal that is in sealing contact with an outer circumferential surface of the protective tube, the protective tube being slidable relative to the seal.

10. A catheter comprising:
a sheath configured to be inserted into a lumen in a living body, the sheath possessing a proximal portion;
a drive shaft positioned in the sheath to transmit a mechanical drive force;
an axially movable hub connected to the drive shaft so that axial movement of the hub results in axial movement of the drive shaft;
an outer tube positioned proximal of the sheath, the drive shaft passing through the outer tube, the outer tube possessing a proximal portion at which is located a first connector, the outer tube possessing a distal portion;
an axially movable inner tube connected to the hub to axially move together with the hub relative to the outer tube, the inner tube being positioned inside the outer tube and projecting in a distal direction from the hub, the inner tube possessing a distal end;
a second connector connected to and disconnectable from the first connector, the second connector comprising a pass-through port, the inner tube and the drive shaft both passing through the pass-through port of the second connector;
a sheath connection portion connecting the proximal portion of the sheath and the distal portion of the outer tube, the drive shaft passing through the sheath connection portion;
a protective tube fixed to and axially movable together with one of the hub and the inner tube, the protective tube axially overlapping and surrounding a portion of the drive shaft, the protective tube possessing an outer peripheral surface and a distal end that protrudes distally beyond a distal end of the inner tube, the drive shaft being accommodated in the protective tube, the protective tube being positioned inside the outer tube and being removable from inside the outer tube together with the hub and the inner tube after the second connector is disconnected from the first connector; and
a seal in sealing contact with the outer peripheral surface of the protective tube, the drive shaft passing through the seal, the protective tube and the drive shaft being removable from the seal.

11. The catheter according to claim 10, wherein the seal is located in the sheath connection portion, the seal being positioned between a distal-most end of the outer tube and a proximal-most end of the sheath.

12. The catheter according to claim 10, wherein the seal possesses a—passage through which the protective tube passes, the seal being configured so that the passage automatically closes when the protective tube and the drive shaft are removed from the seal.

13. The catheter according to claim 10, further comprising an engagement portion at a distal portion of the inner tube, the engagement portion possessing an outer diameter that is enlarged relative to an outer diameter of an immediately adjoining portion of the inner tube, the pass-through port of the second connector possessing an inner diameter smaller than the outer diameter of the engagement portion so that the engagement portion axially moving in the proximal direction relative to the second connector is unable to pass through the pass-through port.

14. The catheter according to claim 10, wherein the outer tube possesses an inner circumferential surface that slopes inwardly in a distal direction.

15. The catheter according to claim 10, wherein the sheath connection portion possesses an inner circumferential surface that slopes inwardly in a distal direction.

16. The catheter according to claim 10, wherein the sheath includes a lumen to receive the drive shaft, the sheath possessing a distal end portion at which is located a guide wire lumen that is axially offset from the lumen in the sheath.

17. A method comprising:

inserting a sheath of a catheter into a lumen in a living body, the sheath possessing a lumen extending along a length of the sheath, the catheter also comprising: a drive shaft positioned in the lumen of the sheath to transmit a mechanical drive force; an outer tube positioned proximal of the sheath and comprising a first connector at a proximal portion of the outer tube, the outer tube possessing a lumen; an axially movable inner tube positioned at least partially inside the outer tube, the inner tube possessing a distal end; a second connector connected to the first connector and comprising a pass-through port through which the inner tube and the drive shaft pass; a sheath connection portion connecting the sheath and the outer tube; and a protective tube protruding distally beyond the distal end of the inner tube, the protective tube surrounding a portion of the drive shaft, the protective tube being positioned inside the outer tube and inside the sheath;

moving the sheath to a target site in the living body;

disconnecting the second connector from the first connector while the sheath remains in the living body;

proximally moving the drive shaft, the inner tube and the protective tube relative to the outer tube to remove the drive shaft, the inner tube and the protective tube from the outer tube while the sheath remains in the living body; and inserting a wire into the outer tube while the sheath remains in the living body; and axially moving the wire through the outer tube, through the sheath connection portion and into the lumen of the sheath while the sheath remains in the living body.

18. The method according to claim 17, wherein the sheath of the catheter is inserted into the lumen in the living body by first passing a guide wire through a guide wire lumen at a distal end of the sheath and advancing the guide wire into the lumen in the living body, and then moving the sheath along the guide wire to insert the sheath into the lumen in the living body.

19. The method according to claim 17, further comprising, after moving the sheath to the target site in the living body and before disconnecting the second connector from the first connector, axially moving and rotating an ultrasound transducer which transmits and receives ultrasounds to obtain information used to form images of the lumen in the living body.

20. The method according to claim 17, wherein the wire is guided into the lumen of the sheath by a sloping inner circumferential surface that slopes inwardly in a distal direction, the sloping inner circumferential surface being part of the outer tube or part of the sheath connection portion.

* * * * *